United States Patent
Downey et al.

(10) Patent No.: US 11,634,680 B2
(45) Date of Patent: Apr. 25, 2023

(54) PROCESS AND SYSTEM FOR PROPAGATING CELL CULTURES WHILE PREVENTING LACTATE ACCUMULATION

(71) Applicant: LONZA LTD, Visp (CH)

(72) Inventors: Brandon John Downey, Visp (CH); John Michael Schmitt, Visp (CH); Jeffrey Francis Breit, Visp (CH)

(73) Assignee: LONZA LTD, Visp (CH)

( * ) Notice: Subject to any disclaimer, the term of this patent is extended or adjusted under 35 U.S.C. 154(b) by 360 days.

(21) Appl. No.: 16/765,346

(22) PCT Filed: Nov. 20, 2018

(86) PCT No.: PCT/US2018/061912
§ 371 (c)(1),
(2) Date: May 19, 2020

(87) PCT Pub. No.: WO2019/100040
PCT Pub. Date: May 23, 2019

(65) Prior Publication Data
US 2020/0354666 A1    Nov. 12, 2020

Related U.S. Application Data

(60) Provisional application No. 62/747,311, filed on Oct. 18, 2018, provisional application No. 62/588,464, filed on Nov. 20, 2017.

(51) Int. Cl.
*C12M 1/34* (2006.01)
*C12M 1/36* (2006.01)

(52) U.S. Cl.
CPC ............ *C12M 41/32* (2013.01); *C12M 41/48* (2013.01)

(58) Field of Classification Search
CPC .............................. C12M 41/32; C12M 41/48
See application file for complete search history.

(56) References Cited

U.S. PATENT DOCUMENTS

| 11,384,378 | B2 * | 7/2022 | Goudar | C12N 5/0018 |
| 2017/0130186 | A1 * | 5/2017 | Berry | C12M 41/48 |
| 2019/0211294 | A1 * | 7/2019 | Karnieli | C12M 41/12 |

FOREIGN PATENT DOCUMENTS

| EP | 1816188 | 8/2007 |
| WO | 2007085880 | 6/2007 |

OTHER PUBLICATIONS

Craven et al: "Glucose concentration control of a fed-batch mammalian cell bioprocess using a nonlinear model predictive controller," Journal of Process Control, vol. 24, No. 4, Mar. 21, 2014.
(Continued)

*Primary Examiner* — Michael L Hobbs
(74) *Attorney, Agent, or Firm* — Medler Ferro Woodhouse & Mills PLLC

(57) ABSTRACT

A predictive model is described that can predict parameter concentrations in the future based on initial, measured concentrations and historical data. A plurality of multivariate techniques can be used to construct the predictive model capable of forecasting concentrations over multiple and diverse cell lines. The predictive model is also scalable. In one embodiment, a future lactate concentration trajectory is determined and at least one condition within a bioreactor is changed or modified to maintain lactate concentration within desired ranges.

28 Claims, 19 Drawing Sheets

(56) References Cited

OTHER PUBLICATIONS

Le et al., Multivariate analysis of cell culture bioprocess data—Lactate consumption as process indicator, J Biotechnol, 2012, 162(2-3):210-223.

* cited by examiner

PROCESS AND SYSTEM FOR PROPAGATING CELL CULTURES WHILE PREVENTING LACTATE ACCUMULATION

RELATED APPLICATIONS

The present application is based upon and claims priority to U.S. Provisional Patent Application Ser. No. 62/588,464, filed on Nov. 20, 2017, and U.S. Provisional Patent Application Ser. No. 62/747,311, filed on Oct. 18, 2018, which are both incorporated herein by reference.

BACKGROUND

Bioreactors, which are apparatuses in which biological reactions or processes can be carried out on a laboratory or industrial scale, are used widely within the biopharmaceutical industry. Bioreactors can be used to produce all different types of bioproducts. Bioproducts can include, for instance, cell cultures and materials derived from cell cultures including beverages, biofuels, bioenergy, biochemicals, antibiotics, amino acids, enzymes, monoclonal antibodies, monomers, proteins, food cultures, biopolymers, alcohols, flavorings, fragrances, and the like. In some embodiments, cell cultures can be grown for cell therapy. Cell therapy is the prevention, treatment, cure or mitigation of disease or injuries in humans by the administration of autologous, allogeneic or xenogeneic cells that have been manipulated or altered ex vivo. One goal of cell therapy is to repair, replace or restore damaged tissues or organs.

Cell cultures are typically grown in batch processes where the biological material remains in the bioreactor until the end of the reaction time. In certain of these processes, fluid medium contained within the bioreactor can be periodically or continuously removed and resupplied in order to replenish nutrients contained within the fluid medium and for possibly removing damaging by-products that are produced during the process.

During the growth of cell cultures, the regulation of key metabolites in the medium can have a direct impact on the quality of the product that is produced. For example, lactate concentration has long been regarded as one of the key metabolites to control during the growth of cell cultures, especially mammalian cell cultures. Typically, great amounts of lactate are produced during the exponential growth phase of the cell culture, while consumption is observed when the cells enter a stationary phase. High levels of lactate can have many negative impacts on cell culture processes. Lactate accumulation, for instance, can be correlated with negative impact in product quality and attributes. In fact, extreme lactate accumulation in a cell culture can render a cell culture commercially unusable.

Lactate behavior in cell cultures, however, is very unpredictable. Those skilled in the art, for instance, have attempted to monitor and control lactate levels with little success as the mechanisms involved in modulating lactate production and consumption in cell cultures remain unclear and unknown. The highly multivariate, nonlinear and time-varying nature of cell metabolic behavior makes it difficult to both identify and correct the driving forces behind lactate concentration.

Historically, upstream bioprocesses have been monitored by removing samples that are then analyzed for selected metabolites, such as lactate levels. In the past, repeated lactate concentration measurements have been taken in order to predict whether the cell culture will end in a lactate accumulated state and thus a decreased product concentration. Unfortunately, previous lactate concentration calculations only spot problems associated with lactate accumulation too late in the process to enact feed metabolite or operating condition.

Recently, those skilled in the art have attempted to design predictive control models as a quality control tool used during the production of bioproducts. An overview of commercially available model predictive control technology, for instance, is disclosed in an article entitled "A survey of industrial model predictive control technology" by Quin et al., which is incorporated herein by reference. Zupke et al., published an article entitled "Real-time product attribute control to manufacture antibodies with defined N-linked Glycan levels" and discusses using nonlinear model predictive control. Sommeregger et al., published an article entitled "Quality by control: towards model predictive control of mammalian cell culture bioprocesses" which is directed to implementing process analytical technology to move to a more flexible quality design approach. The above articles, however, fail not only to disclose a lactate concentration control system but also fail to provide robust control of process parameters coupled with feedback mechanisms.

In view of the above, a need currently exists for an improved process and system for monitoring biochemical and biopharmaceutical processes such as processes for propagating cell cultures that allows for continuous or periodic adjustments in order to maintain optimum conditions within a bioreactor. A need exists, for instance, for a process and system capable of predicting a quality attribute concentration in a cell culture and maintaining that quality attribute within desired limits. In particular, a need exists for a process and system capable of not only predicting future lactate concentrations in a growing cell culture but also capable of modifying one or more bioreactor controls and/or inputs in order to maintain lactate concentrations within preset limits. A need also exists for an improved process and system for preventing lactate accumulation in cell cultures.

SUMMARY

The present disclosure is generally directed to a process and system for propagating biomaterials, such as cell cultures. In one embodiment, for instance, the process and system of the present disclosure is directed to propagating mammalian cell cultures. In accordance with the present disclosure, a controller containing a predictive model has been developed capable of determining robust quality attribute concentrations, such as lactate concentrations, over an entire incubation period of the cell culture. The predictive model can be used to selectively change at least one condition within the cell culture during propagation in order to maintain the quality attribute concentrations within preset limits. For example, through the process and system of the present disclosure, cell cultures can be propagated in a manner that prevents against lactate accumulation within the cell culture at the end of the process.

In one embodiment, for instance, the present disclosure is directed to a process for propagating a cell culture. The process includes determining a concentration of lactate in the cell culture. In addition, at least one lactate influencing parameter within the cell culture is measured. The lactate concentration and the at least one lactate influencing parameter measurement are sent to a controller. In accordance with the present disclosure, the controller includes a predictive model that determines a future concentration of lactate in the cell culture. At least one condition within the cell culture is then selectively changed based upon the determined future concentration of lactate in the cell culture for maintaining lactate concentration within preset limits.

As described above, in one embodiment, the present disclosure is particularly directed to controlling lactate concentration in a cell culture. It should be understood, however, that the process and system of the present disclosure can be used to monitor and control any suitable quality attribute within the cell culture. The quality attribute may comprise in addition to lactate, protein, cell growth rate, glycan composition, a charge variant, an aggregate, a clipping, disulfide oxidation, or a disulfide shuffling variant. As described below, the system and process is particularly well suited for maintaining lactate concentrations within preset limits.

In one embodiment, the cell culture has an incubation period prior to being harvested. The incubation period, for instance, can be from about 12 hours to about 28 days. Lactate concentrations can be measured at the beginning of the incubation period and fed to the controller. Based on initial lactate concentrations, the controller can then forecast lactate concentrations through the end of the incubation period. The controller can also be configured to determine corrective action for changing at least one condition in the cell culture in order to maintain lactate concentration within preset limits. For instance, lactate concentration information can be determined for about 12 hours to about 4 days prior to the controller determining a future concentration of lactate in the cell culture and making any corrective action. For example, the lactate concentration can be measured for from about 5% to about 40% of the incubation period prior to the controller making lactate forecast determinations. Lactate concentrations can be measured and fed to the controller during the entire incubation period allowing the controller to continue make future predications and make adjustments as needed within the cell culture.

As described above, in addition to lactate concentration, at least one lactate influencing parameter is also measured and fed to the controller. The lactate influencing parameter, for instance, may comprise pH, glutamate concentration, glucose concentration, asparagine concentration, temperature, or nutrient feed rate. In one embodiment, at least two lactate influencing parameters, such as at least three lactate influencing parameters are measured and the measured data are sent to the controller for use in determining a future concentration of lactate in the cell culture.

In one embodiment, the at least one condition that is selectively changed in the cell culture during the process in order to control lactate concentration is the nutrient media being fed to the cell culture. For example, the components of the nutrient media may be changed and/or the flow rate of the nutrient media may be changed in order to influence lactate levels. The nutrient media, for instance, may contain a carbohydrate source, an amino acid source, a vitamin, a lipid, a protein, a peptide, or mixtures thereof.

In one embodiment, the at least one condition that is changed within the cell culture in order to control lactate concentration is the pH of the cell culture. In yet another embodiment, the pH of the cell culture and the nutrient media are both changed and controlled in order to control lactate levels.

The system and process of the present disclosure can be used to control any suitable cell culture. In one embodiment, the cell culture contains mammalian cells. For instance, the cell culture can be used for recombinant protein production.

The predictive model contained within the controller that forecasts lactate concentration can be based on comparing lactate concentration to prior reference data. Future concentration of lactate can be determined by varying the lactate influencing parameter (s) of the predictive model to minimize the square deviation of the lactate concentration predictions from a prescribed reference trajectory. In one embodiment, the predictive model can include weighting in order to further improve results. For example, in one embodiment, weighting can be applied to the difference between the predicted output and the referenced trajectory. In one embodiment, for instance, the weighting can be applied based on the period of time being measured. For instance, greater weighting may be applied to data early in the growth cycle as opposed to data collected later in the growth cycle.

The predictive model contained within the controller can use various multivariate methods in predicting lactate concentration and lactate state in the future. For example, the future lactate state can be determined by the controller from one or more techniques selected from partial least squares analysis, classification trees, support vector machines, linear discriminant analysis and the like. In one embodiment, the predictive model includes at least two multivariate methods in predicting future lactate state. For example, the predictive model can include at least two of the neural network analysis, support vector machines, and latent variable modeling. In one embodiment, the controller uses a reduced order time varying autoregressive exogenous model to predict future lactate concentration.

Through the process of the present disclosure, lactate levels can be monitored and controlled so that the cell culture does not exhibit lactate accumulation at the end of the incubation period. In one embodiment, for instance, the system can include a classification model that predicts if the cell culture ends in a lactate consuming state or a lactate producing state. In addition, the controller can include a dynamic model that can forecast out prescribed concentrations of lactate for future days, potentially through the end of the incubation period of the cell culture. The dynamic model can be provided with different values of lactate influencing parameters to run numerical predictions for determining the best strategy for making any corrective action during growth of the cell culture. In one embodiment, the processing system can be designed such that the bioculture ends within a particular lactate concentration range. For instance, the lactate concentration at the end of the incubation period can be less than about 2 g/L, such as less than about 1.5 g/L, such as less than about 1 g/L.

The above lactate concentration ranges are merely exemplary. The process and system of the present disclosure can be tailored to any particular application. For instance, although a high lactate concentration may be undesirable, lower lactate concentrations may also be undesirable as well. The process and system of the present disclosure can control the metabolic state of the cell culture as opposed to simply controlling lactate concentration. For instance, in one embodiment, the process and system of the present disclosure may control the slope of lactate concentration over time as opposed to merely controlling the final lactate concentration.

The present disclosure is also directed to a system for propagating a cell culture. The system includes a bioreactor defining a hollow interior for receiving a cell culture. The bioreactor includes a plurality of ports for feeding and/or removing materials from the hollow interior. A nutrient media feed for feeding nutrient media to the hollow interior of the bioreactor is in fluid communication with at least one of the ports on the bioreactor. The system further includes a controller that is configured to receive lactate concentration measurements of a cell culture contained in the bioreactor. The controller is also configured to receive measurements of at least one lactate influencing parameter. The controller includes a predictive model that determines a future concentration of lactate in a cell culture contained in the bioreactor. For instance, the predictive model can be configured to forecast lactate concentration throughout the entire incubation period of the cell culture. The controller is configured to control the nutrient media feed for selectively increasing or decreasing flow of a nutrient media into the bioreactor based on the predicted lactate concentration for maintaining the lactate concentration within preset limits.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
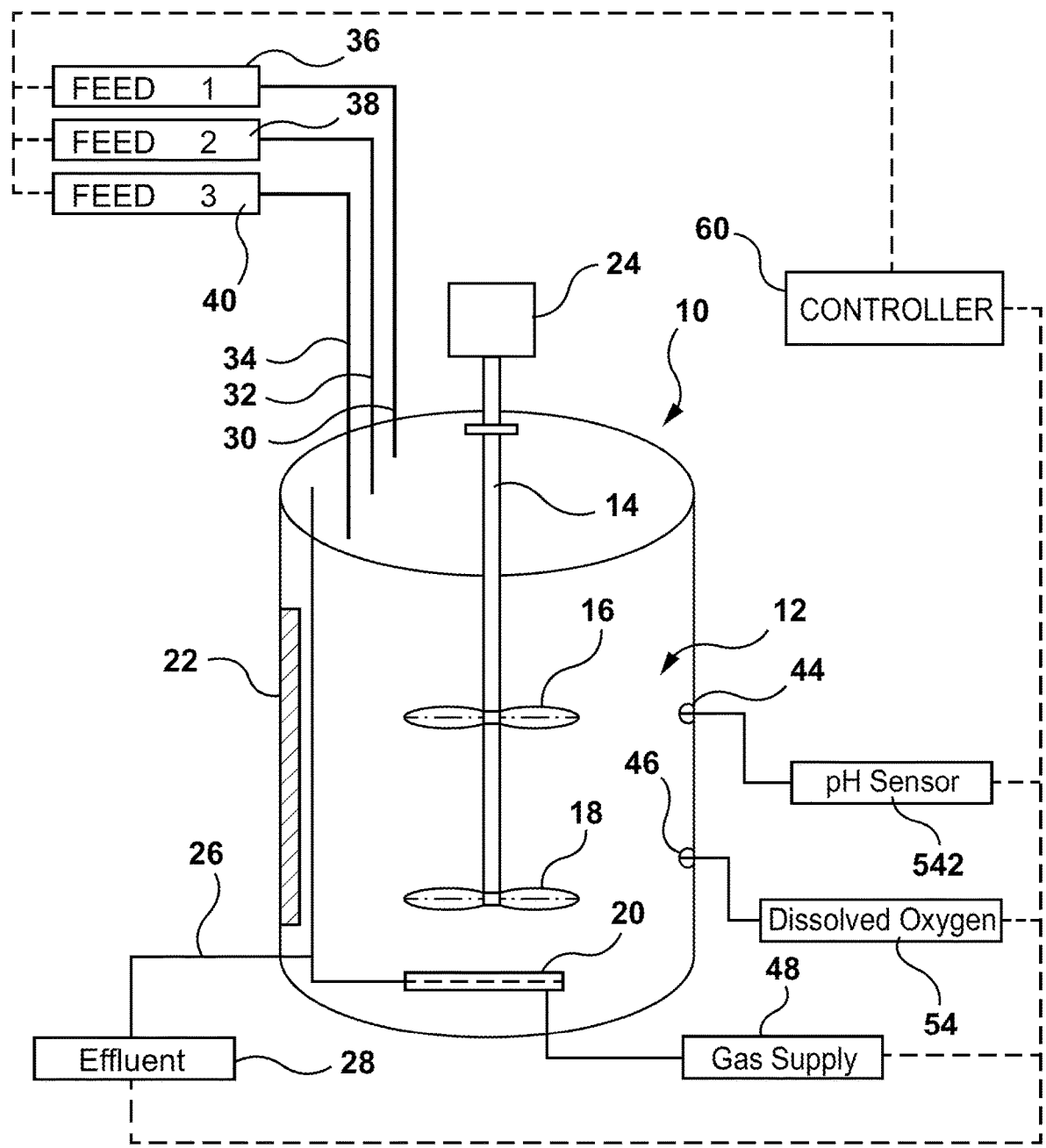
FIG. 1 is a cross sectional view of one embodiment of a bioreactor system in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a process and system for producing a bioproduct. In one embodiment, for instance, the present disclosure is directed to a process and system for propagating a cell culture within a bioreactor. The system of the present disclosure can use open loop or closed loop control for monitoring a quality attribute, such as one or more parameters in the bioreactor and then automatically changing or varying the flow of a parameter influencing substance into or out of the bioreactor.

In general, any suitable quality attribute can be monitored and controlled within a cell culture in accordance with the present disclosure. In one embodiment, the system includes a predictive control module that can be inputted with not only actual cell culture measurements but also reference data from previous cell cultures. Based upon the inputted information, the predictive model can use multivariate analysis in order to calculate future concentrations of one or more quality attributes within a cell culture. For example, in one embodiment, the predictive model uses two different multivariate analysis methods in computing future concentration levels.

The quality attribute monitored and controlled in accordance with the present disclosure can vary depending upon the particular application and the desired result. For instance, quality attributes that can be controlled include protein titer, cell growth rate, and glycan composition. Glycan composition can include galactosylation, high mannose species, sialation and fucosylation. In another embodiment, the quality attribute being controlled may comprise a charge variant. For instance, the charge variant may relate to C-terminal lysine cleavage, deamidation, adduct formation, succinide formation, oxidation, C-terminal proline amidation, isomerization, and/or sialation. Still other quality attributes that can be controlled include aggregate concentration, clipping, disulfide oxidation, and a disulfide shuffling variant.

In one embodiment, the process and system of the present disclosure is particularly directed to monitoring and controlling lactate concentration within a cell culture. In accordance with the present disclosure, a predictive model is established that is capable of determining a future lactate concentration trajectory within the cell culture based upon initial lactate concentration data. The future lactate concentration can be determined early in the cell culture process allowing for manual or automatic controls of one or more conditions within the bioreactor in order to maintain lactate concentration within preset limits. Through the process and system of the present disclosure, for instance, lactate accumulation can be prevented within the cell culture over the course of the incubation period and prior to harvesting the cell culture.

Of particular advantage, the process and system of the present disclosure can be scaled to various different bioreactor sizes and to various cell lines. For instance, the predictive models used in accordance with the present disclosure are robust and developed for platform processes that are not cell line dependent and thus can be used in clinical as well as commercial manufacturing. All different bioproducts can be produced in accordance with the present disclosure. For example, the system and the process can be adapted to any cell culture being propagated within a bioreactor. In one embodiment, the cell culture contains mammalian cells. Mammalian cells are very frequently used for the production of complex biopharmaceuticals. For instance, mammalian cells can be used for recombinant protein production. The system and process of the present disclosure, for instance, can directly impact and improve both product yield and product quality leading to increased titer concentration.

In one example, the system and process of the present disclosure are used to produce bio-therapeutic proteins from genetically modified mammalian cells within the bioreactor. Such production can be from cell lines of established cell cultures, such as, for example, CHO, NSO, or PER.C6. These cells express the protein of interest and subsequently secrete the protein into the media. The cell culture can be grown in a fed-batch process which, as used herein, also includes perfusion type cell culture systems where fluid is periodically or continuously removed from the bioreactor or non-perfusion systems.

Referring to FIG. 1, one embodiment of a bioreactor system in accordance with the present disclosure is shown. The bioreactor system includes a bioreactor 10. In general, the system and process of the present disclosure can use any suitable bioreactor. The bioreactor, for instance, may comprise a fermenter, a stirred-tank reactor, an adherent bioreactor, a wave-type bioreactor, a disposable bioreactor, and the like. In the embodiment illustrated in FIG. 1, the bioreactor 10 comprises a hollow vessel or container that includes a bioreactor volume 12 for receiving a cell culture within a fluid growth medium. As shown in FIG. 1, the bioreactor system can further include a rotatable shaft 14 coupled to an agitator such as dual impellers 16 and 18.

The bioreactor 10 can be made from various different materials. In one embodiment, for instance, the bioreactor 10 can be made from metal, such as stainless steel. Metal bioreactors are typically designed to be reused.

Alternatively, the bioreactor 10 may comprise a single use bioreactor made from a rigid polymer or a flexible polymer film. When made from a rigid polymer, for instance, the bioreactor walls can be free standing. Alternatively, the bioreactor can be made from a flexible polymer film or shape conforming material that can be liquid impermeable and can have an interior hydrophilic surface. In one embodiment, the bioreactor 10 can be made from a flexible polymer film that is designed to be inserted into a rigid structure, such as a metal container for assuming a desired shape. Polymers that may be used to make the rigid vessel or flexible polymer film include polyolefin polymers, such as polypropylene and polyethylene. Alternatively, the polymer can be a polyamide. In still another embodiment, a flexible polymer film can be formed from multiple layers of different polymer materials. In one embodiment, the flexible polymer film can be gamma irradiated.

The bioreactor 10 can have any suitable volume. For instance, the volume of the bioreactor 10 can be from 0.1 mL to about 25,000 L or larger. For example, the volume 12 of the bioreactor 10 can be greater than about 0.5 L, such as greater than about 1 L, such as greater than about 2 L, such as greater than about 3 L, such as greater than about 4 L, such as greater than about 5 L, such as greater than about 6 L, such as greater than about 7 L, such as greater than about 8 L, such as greater than about 10 L, such as greater than about 12 L, such as greater than about 15 L, such as greater than about 20 L, such as greater than about 25 L, such as greater than about 30 L, such as greater than about 35 L, such as greater than about 40 L, such as greater than about 45 L. The volume of the bioreactor 10 is generally less than about 25,000 L, such as less than about 15,000 L, such as less than about 10,000 L, such as less than about 5,000 L, such as less than about 1,000 L, such as less than about 800 L, such as less than about 600 L, such as less than about 400 L, such as less than about 200 L, such as less than about 100 L, such as less than about 50 L, such as less than about 40 L, such as less than about 30 L, such as less than about 20 L, such as less than about 10 L. In one embodiment, for instance, the volume of the bioreactor can be from about 1 L to about 5 L. In an alternative embodiment, the volume of the bioreactor can be from about 25 L to about 75 L. In still another embodiment, the volume of the bioreactor can be from about 1,000 L to about 5,000 L.

In addition to the impellers 16 and 18, the bioreactor 10 can include various additional equipment, such as baffles, spargers, gas supplies, heat exchangers or thermal circulator ports, and the like which allow for the cultivation and propagation of biological cells. For example, in the embodiment illustrated in FIG. 1, the bioreactor 10 includes a sparger 20 and a baffle 22. The sparger 20 is in fluid communication with a gas supply 48 for supplying gases to the bioreactor 10, such as carbon dioxide, oxygen and/or air. In addition, the bioreactor system can include various probes for measuring and monitoring pressure, foam, pH, dissolved oxygen, dissolved carbon dioxide, and the like.

As shown in FIG. 1, the bioreactor 10 can include a rotatable shaft 14 attached to impellers 16 and 18. The rotatable shaft 14 can be coupled to a motor 24 for rotating the shaft 14 and the impellers 16 and 18. The impellers 16 and 18 can be made from any suitable material, such as a metal or a biocompatible polymer. Examples of impellers suitable for use in the bioreactor system include hydrofoil impellers, high-solidity pitch-blade impellers, high-solidity hydrofoil impellers, Rushton impellers, pitched-blade impellers, gentle marine-blade impellers, and the like. When containing two or more impellers, the impellers can be spaced apart along the rotating shaft 14.

As shown in FIG. 1, the bioreactor 10 also includes a plurality of ports. The ports can allow supply lines and feed lines into and out of the bioreactor 10 for adding and removing fluids and other materials. In addition, the one or more ports may be for connecting to one or more probes for monitoring conditions within the bioreactor 10. In addition, the bioreactor 10 and be placed in association with a load cell for measuring the mass of the culture within the bioreactor.

In the embodiment illustrated in FIG. 1, the bioreactor 10 includes a bottom port 26 connected to an effluent 28 for withdrawing materials from the bioreactor continuously or periodically. In addition, the bioreactor 10 includes a plurality of top ports, such as ports 30, 32, and 34. Port 30 is in fluid communication with a first fluid feed 36, port 32 is in fluid communication with a second feed 38 and port 34 is in fluid communication with a third feed 40. The feeds 36, 38 and 40 are for feeding various different materials to the bioreactor 10, such as a nutrient media. As used herein, a nutrient media refers to any fluid, compound, molecule, or substance that can increase the mass of a bioproduct, such as anything that may be used by an organism to live, grow or otherwise add biomass. For example, a nutrient feed can include a gas, such as oxygen or carbon dioxide that is used for respiration or any type of metabolism. Other nutrient media can include carbohydrate sources. Carbohydrate sources include complex sugars and simple sugars, such as glucose, maltose, fructose, galactose, and mixtures thereof. A nutrient media can also include an amino acid. The amino acid may comprise, glycine, alanine, valine, leucine, isoleucine, methionine, proline, phenylalanine, tryptophan, serine, threonine, asparagine, glutamine, tyrosine, cysteine, lysine, arginine, histidine, aspartic acid and glutamic acid, single stereoisomers thereof, and racemic mixtures thereof. The term "amino acid" can also refer to the known non-standard amino acids, e.g., 4-hydroxyproline, ε-N,N,N-trimethyllysine, 3-methylhistidine, 5-hydroxylysine, O-phosphoserine, γ-carboxyglutamate, γ-N-acetyllysine, ω-N-methylarginine, N-acetylserine, N,N,N-trimethylalanine, N-formylmethionine, γ-aminobutyric acid, histamine, dopamine, thyroxine, citrulline, ornithine, β-cyanoalanine, homocysteine, azaserine, and S-adenosylmethionine. In some embodiments, the amino acid is glutamate, glutamine, lysine, tyrosine or valine.

The nutrient media can also contain one or more vitamins. Vitamins that may be contained in the nutrient media include group B vitamins, such as B12. Other vitamins include vitamin A, vitamin E, riboflavin, thiamine, biotin, and mixtures thereof. The nutrient media can also contain one or more fatty acids and one or more lipids. For example, a nutrient media feed may include cholesterol, steroids, and mixtures thereof. A nutrient media may also supply proteins and peptides to the bioreactor. Proteins and peptides include, for instance, albumin, transferrin, fibronectin, fetuin, and mixtures thereof. A growth medium within the present disclosure may also include growth factors and growth inhibitors, trace elements, inorganic salts, hydrolysates, and mixtures thereof. Trace elements that may be included in the growth medium include trace metals. Examples of trace metals include cobalt, nickel, and the like.

As shown in FIG. 1, the bioreactor can be in communication with multiple nutrient feeds. In this manner, a nutrient media can be fed to the bioreactor containing only a single nutrient for better controlling the concentration of the nutrient in the bioreactor during the process. In addition or alternatively, the different feed lines can be used to feed gases and liquids separately to the bioreactor.

In addition to ports on the top and bottom of the bioreactor 10, the bioreactor can include ports located along the sidewall. For instance, the bioreactor 10 shown in FIG. 1 includes ports 44 and 46.

Ports 44 and 46 are in communication with a monitoring and control system that can maintain optimum concentrations of one or more parameters in the bioreactor 10 for propagating cell cultures or otherwise producing a bioproduct. In the embodiment illustrated, for example, port 44 is associated with a pH sensor 52, while port 46 is associated with a dissolved oxygen sensor 54. The pH sensor 52 and the dissolved oxygen sensor 54 are in communication with a controller 60. The system of the present disclosure can be configured to allow for the determination and the measurements of various parameters within a cell culture contained within the bioreactor 10. Some of the measurements can be made in line, such as pH and dissolved oxygen. Alternatively, however, measurements can be taken at line or off line. For example, in one embodiment, the bioreactor 10 can be in communication with a sampling station. Samples of the cell culture can be fed to the sampling station for taking various measurements. In still another embodiment, samples of the cell culture can be removed from the bioreactor and measured off line.

In accordance with the present disclosure, a plurality of parameters can be measured during growth of a cell culture within the bioreactor 10. In general, the parameter being controlled by the process and system of the present disclosure is measured in conjunction with one or more other parameters that can influence the concentration of the parameter being controlled. For example, in one embodiment, lactate concentration is measured within the cell culture in conjunction with at least one other lactate influencing parameter. The lactate influencing parameter can comprise, for instance, glutamate concentration, glucose concentration, an amino acid concentration such as asparagine concentration, or the like. In one embodiment, at line or off line analysis of the cell culture can be performed using any suitable instruments such as a NOVA Bioprofile 400 analyzer sold by Nova Biomedical. The above analyzer is capable of measuring lactate concentration in conjunction with one or more of the lactate influencing parameters.

In accordance with the present disclosure, the lactate concentration and the concentration of the one or more lactate influencing parameters in addition to various other conditions in the bioreactor can be fed to the controller 60. The controller includes a control model that, based on the inputted data, is capable of forecasting lactate concentration in the future as the cell culture continues to propagate. In one embodiment, for instance, the controller can provide an early warning system that produces a percent probability as to whether the lactate concentration at the end of the cell culture incubation period is within preset limits or if the cell culture will end in a lactate accumulating state. The controller 60 can also be configured to accurately predict lactate concentration into the future. For instance, in one embodiment, the controller can forecast a lactate concentration trajectory that predicts lactate concentration through the entire incubation period until the cell culture is harvested. In one embodiment, the controller can also be configured to suggest or automatically implement corrective actions in case lactate concentration is not within preset limits. For example, the controller can be configured to determine nutrient feed changes, or changes in other operating conditions that may be required to drive the lactate concentration to a desired value. In order to determine corrective actions, the controller may run multiple iterations for determining future lactate concentrations based on altering one or more conditions within the bioreactor until an optimized change in one or more conditions is selected.

The controller 60 may comprise one or more programmable devices or microprocessors. As shown in FIG. 1, the controller 60 can be in communication with the one or more feeds 36, 38 and 40 and with one or more effluents 28. In addition, the controller 60 can be in communication with the pH sensor 52, the dissolved oxygen sensor 54, and the gas supply 48 that feeds gas to the sparger 20. The controller 60 can be configured to increase or decrease the flow of materials into and out of the bioreactor 10 based upon the lactate concentration and the concentration of one or more lactate influencing parameters. In this manner, the controller 60 can maintain lactate concentration within preset limits. The controller 60 can operate in an open loop control system or can operate in a closed loop control system, where adjustments to input and/or output devices are completely automated. In other embodiments, the controller 60 can suggest corrective actions in order to influence lactate concentration and the corrective actions can be done manually.

Figure 2:
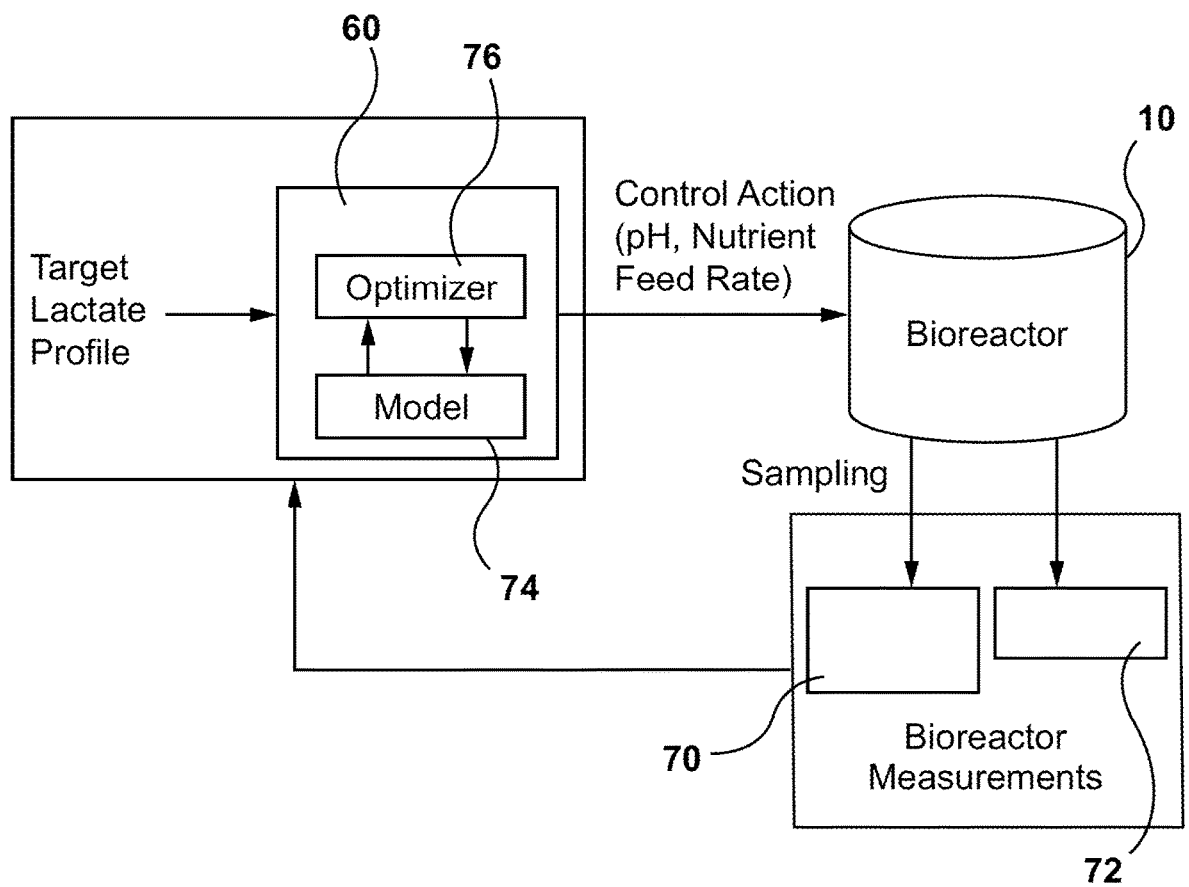
FIG. 2 is a diagram illustrating one embodiment of a control system in accordance with the present disclosure.

Referring to FIG. 2, one embodiment of a bioreactor system in accordance with the present disclosure is illustrated. As shown, a cell culture is cultivated in the bioreactor 10 for an incubation period and then harvested. During the incubation, various parameters in the bioreactor 10 are monitored. The parameters are measured by one or more analyzers 70. In accordance with the present disclosure, the analyzer 70 periodically or continuously monitors lactate concentration which is communicated to the controller 60. In order for the controller 60 to predict future lactate concentrations within the cell culture, at least one other lactate influencing parameter is also measured and fed to the controller 60. The lactate influencing parameter that is measured may include the pH of the cell culture, glutamate concentration, glucose concentration, asparagine concentration, temperature and/or nutrient feed rate. In one embodiment, at least two lactate influencing parameters are measured during the process, such as at least three lactate influencing parameters, such as at least four lactate influencing parameters. For example, the one or more analyzers 70 may measure from about two lactate influencing parameters to about eight lactate influencing parameters. All of the measured data including the lactate concentration is fed to the controller 60. These parameters can be measured continuously or periodically.

In addition to the real time data measured in the bioreactor 10, reference data 72 from prior cell cultures can also be collected and fed to the controller 60. The use of past reference data can improve future calculations of lactate concentration. For example, the reference data 72 can include lactate concentration trajectories in cell cultures where the lactate influencing parameters have varied greatly which can improve the predictability of the controller 60.

As shown in FIG. 2, the controller 60 can be programmed with a target lactate profile. The controller 60 can include at least one control model 74. In one embodiment, for instance, the controller can include a classification model and a predictive model. The classification model can be configured to produce a percent probability that the incubation period of the cell culture will end in a lactate accumulating state or in a lactate consuming state. The classification model can use various multivariate methods including a partial least squares analysis alone or in combination with a linear discriminant analysis. The classification model may also use classification trees, support vector machines, and the like. In one embodiment, a median of the percent probabilities resulting from each classification model can be employed as the final percent probability for the cell culture. In one embodiment, the percent probability that the cell culture will end in a lactate accumulating state can be presented to a user in order to allow the user to determining if intervention is required during the growth of the cell culture in order to ensure that the incubation period of the cell culture ends with desired lactate concentration limits.

The controller 60 can also include a predictive model. The predictive model can determine a future lactate concentration trajectory over the entire incubation period. In addition, the predictive controller can be configured to predict how changes in one or more conditions within the bioreactor 10 over a specified control horizon will affect lactate concentration over a specified prediction horizon. For example, as shown in FIG. 2, the predictive model 74 can be in communication with an optimizer 76. The optimizer 76 can be configured to simulate results within the bioreactor 10 if one or more conditions are varied. The conditions can include changing nutrient media feed rate and thereby changing glucose concentration, glutamate concentration, asparagine concentration, and the like. In addition to nutrient feed rates, the optimizer 76 can also change various other conditions including pH and gas rate additions. The optimizer 76 can run multiple simulations and numerous iterations in order to determine if corrective action is needed within the cell culture, and, if so, not only the best conditions to change in the bioreactor but the magnitude of the change. The predictive model ultimately determines variations in manipulated variables in order to minimize future deviations of the lactate concentration from a specified referenced trajectory. As future data is fed to the controller 60, the optimizer 76 can continue to run simulations over the entire incubation period in order to further change or tweak manipulated variables thereby changing one or more conditions within the cell culture.

Figure 3:
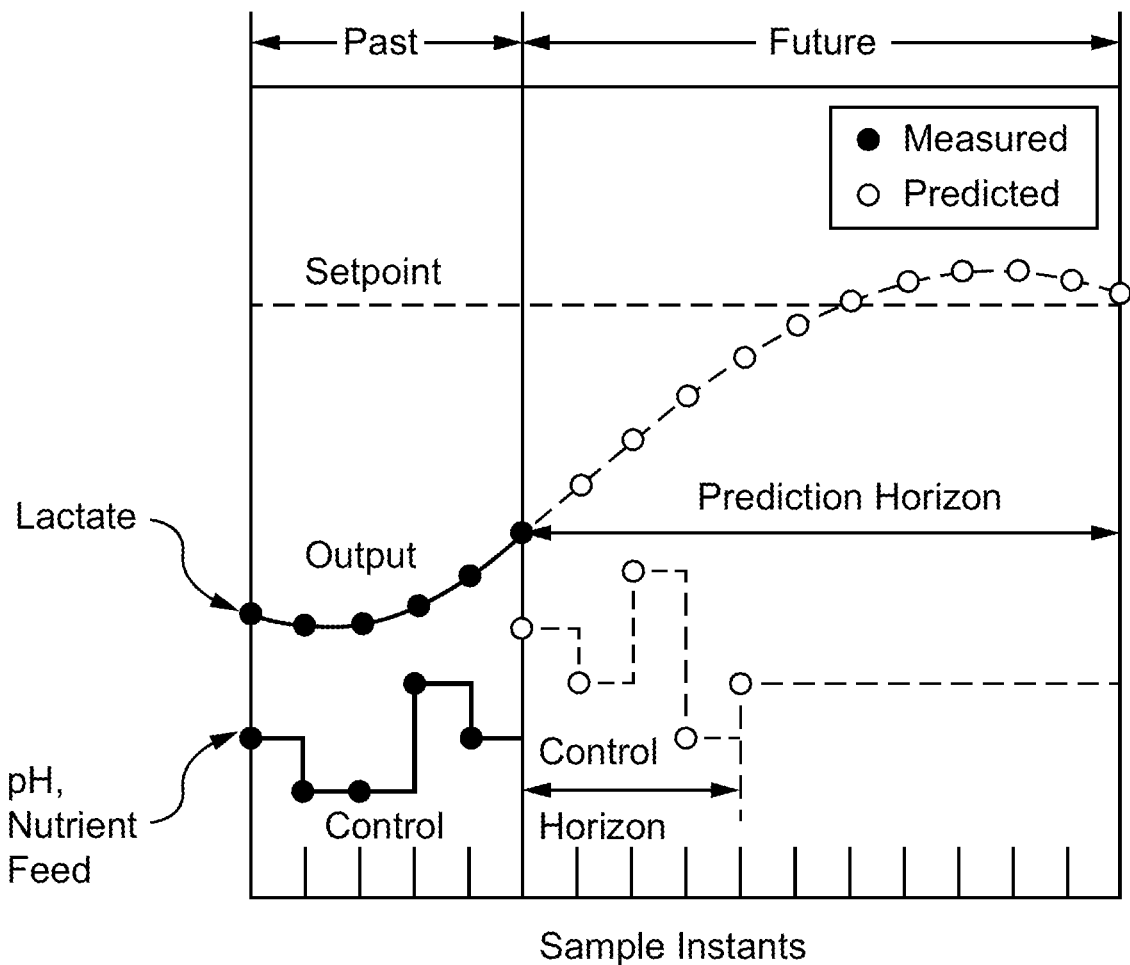
FIG. 3 is a diagram illustrating control of lactate concentration over a cell culture incubation period.

FIG. 3 illustrates one embodiment by which the predictive model 74 and the optimizer 76 may operate within the controller 60. As shown in FIG. 3, various measurements of the cell culture are made and fed to the controller. For instance, the controller can receive lactate concentration information, pH information, and nutrient feed information. The predictive model then calculates or determines a lactate concentration trajectory that results in a prediction horizon. As shown in FIG. 3, the controller 60 can also be preprogrammed with a lactate concentration set point. The set point can be a desired final lactate concentration within the cell culture that indicates the cell culture is not in a lactate accumulation state.

As shown in FIG. 3, the optimizer 76 runs simulations by changing, in this embodiment, the pH and nutrient feed within the cell culture. For example, the optimizer can run simulations based on manipulating pH and nutrient feed over a controlled horizon. Based on changes in pH and nutrient feed, the lactate trajectory over the prediction horizon is recalculated for determining whether one or more conditions within the cell culture need to be changed in order to maintain lactate concentration levels within desired limits. This process can occur continuously or periodically over the entire incubation period. As described above, the controller 60 can be configured to automatically control conditions within the bioreactor or can be designed to alert a user so that a user can make the changes manually.

The predictive model can run simulations and make determinations based on using various multivariate methods. In one embodiment, for instance, the lactate concentration trajectory can be determined by minimizing or optimizing the variations of the lactate influencing parameters in the predictive model in order to minimize weighted squared deviations of lactate concentration predictions from a prescribed reference trajectory and weighted squared deviations and changes in each of the manipulated variables. This optimization can be performed subject to linear inequality constraints depending upon the amount of each manipulated variable can change over time.

In one embodiment, the predictive model can include a predictive control algorithm that employs reduced-order linear models such as a reduced order time varying autoregressive exogenous model (ARX model). Techniques that may be used in the predictive model include a neural network, support vector machines, latent variable modeling including partial least squares analysis. In addition, decision trees and linear discriminant analysis can be used.

In one embodiment, at least two multivariate methods are incorporated into the predictive model. For instance, the predictive model can include at least two of the neural network model, support vector machines, and latent variant modeling in determining lactate concentration predictions.

In one embodiment, the predictive model is a nonlinear ARX model that includes model regressors and a nonlinearity estimator. The nonlinearity estimator can include both linear and nonlinear functions that act on the model regressors to give the model output.

In one embodiment, a reduced-order model is designed that adequately represents the input-output dynamics of the system to be controlled. A set of manipulated variables can be identified that have a strong influence on the output or outputs of interest. Knowledge of the manipulated variable values in conjunction with knowledge of prior output values can be used to predict future behavior. In one embodiment, the relationship between inputs and outputs in a multi-input, single-output ARX formulation is of the form:

$$y(t) = -\Sigma_{i=1}^{n_a} a_i y(t-i) + \Sigma_{j=1}^{n_i} \Sigma_{i=1}^{n_b} b_{ji} u_j(t-n_k-i+1) \tag{1}$$

where y(t) is the output/controlled variable, $u_j(t)$ represents one of $n_i$ manipulated variables, $n_k$ is the time delay, $n_a$ is the number of poles, $n_b$ is the number of zeros, and $a_i$ and $b_{ji}$ are coefficients to be determined via the identification process. In a time-varying ARX model, the coefficients representing the influence of each parameter change with time (i.e. day), such that the model is time-varying. The ARX model as written in (1) is a one-step ahead predictor; the value for the output at day t is determined from prior values of the output as well as current and prior values of the manipulated variables. This model can be extended into a multi-step ahead predictor by using the output prediction from the prior day along with prescribed values for the manipulated variables, such as would be determined by a control strategy, to predict future output values.

In one embodiment, the model parameters can be determined by minimizing any multi-step bootstrap root mean square prediction errors across replicates. In these multi-step simulations, recorded process data can be employed for the manipulated variables while predicted output values from the equation above can be employed for subsequent prediction days.

As described above, in one embodiment, the system and method of the present disclosure are directed to regulating lactate concentration using a manipulated set of variables. In one embodiment, a model predictive controller can prescribe the values for the manipulated variables over a control horizon from knowledge of the desired lactate concentration and prior values of the recorded manipulated variables and lactate concentration. The model predictive controller can employ the time-varying ARX model developed from historical process data to determine the values for the manipulated variables that will result in the lactate concentration reaching the desired value in the future. Lactate predictions are generated in a multi-step fashion over the prediction horizon from a sequence of values for the manipulated variables over the control horizon. Optimal values for the manipulated variables are determined over the control horizon to minimize an objective function involving the deviation of the model output predictions from the desired trajectory over the prediction horizon. Once the optimal sequence of manipulated variables is determined, in one embodiment, only the first of these values can be employed in the bioreactor. In this manner, at the next sampling instant, the lactate concentration is measured and the process repeats. Because the recorded, rather than predicted, lactate concentration is employed in each subsequent optimization cycle, the prediction errors that can accumulate in a multi-step prediction are limited in their impact in the controller implementation.

In one embodiment, the design of a model predictive controller can include specifying a number of design parameters to compute the objective function optimized during the controller operation. For example, in one embodiment, the following algorithm may be used based on least mean squares:

$$J = \Sigma_{i=1}^{P} \{w_i^y(\hat{y}(t+i) - r(t+i))\}^2 + \Sigma_{j=1}^{n_{mv}} \Sigma_{i=1}^{P} \left\{ \frac{w_{i,j}^{\Delta u}}{s_j^u} (u_j(t+i) - u_j(t+i-1)) \right\}^2 \quad (2)$$

wherein:
 P is the number of days in the prediction horizon
 $\hat{y}$ is the predicted value of the lactate concentration from the reduced order model
 r is the value of the lactate concentration for the desired reference trajectory
 $w_i^y$ is the weighting to be applied to the difference between the predicted output and the reference trajectory for each day in the prediction horizon
 $n_{mv}$ is the number of manipulated variables
 $u_j$ is the value of manipulated variable j at a particular day
 $w_{i,j}^{\Delta u}$ is the weighting applied to the difference between subsequent manipulated variable values for manipulated variable j on the $i^{th}$ prediction horizon day
 $s_j^u$ is a scaling factor for the $j^{th}$ manipulated variable, to handle differences in scales between the manipulated variables In one embodiment, the coefficients on the right side of the above equation can be set to 0 to provide the following simplified equation.

$$J = \Sigma_{i=1}^{P} \{w_i^y(\hat{y}(t+i) - r(t+i))\}^2, \quad (3)$$

where: P is the number of days in the prediction horizon; $\hat{y}$ is the predicted value of the lactate concentration from the reduced order model; r is the value of the lactate concentration for the desired reference trajectory; $w_i^y$ is the weighting to be applied to the difference between the predicted output and the reference trajectory for each day in the prediction horizon.

The objective function penalizes differences in the predicted output from the reference trajectory. Different weightings can be employed across the days of the prediction horizon if concern exists regarding multi-step prediction accuracy of the reduced-order model far into the future. The optimal values for the manipulated variables over the control horizon are achieved by minimizing the objective function with respect to both bound and rate constraints on the manipulated variables.

Of particular advantage, the controller 60 of the present disclosure is capable of providing an indication early in the incubation period whether the cell culture will end in a lactate accumulating state. The predictive model, for instance, has been found to be robust so that accurate predictions regarding lactate concentration can be made early in the process that provides ample opportunity to take corrective actions in order to improve the product quality by increasing titer concentration.

For example, the controller can be configured to make initial predictions regarding lactate concentration after less than about 40% of the incubation time, such as less than about 30% of the incubation time, such as less than about 20% of the incubation time, such as less than about 15% of the incubation time, such as less than about 10% of the incubation time, such as even less than about 5% of the incubation time. For example, in one embodiment, the controller can receive periodic lactate concentration information within a cell culture and data regarding at least one other lactate influencing parameter during the initial 12 hours of the cell culture, such as during the initial 2 days of the cell culture, such as during the initial 4 days of the cell culture, and be capable of accurately determining a lactate concentration trajectory in order to determine whether corrective action is needed. For example, in one embodiment, the controller 60 can begin making selective adjustments to at least one condition in the bioreactor after about 12 hours to about 4 days of receiving data and based upon how the data fits within the predictive model.

In order to control lactate concentration in the future, one or more conditions within the bioreactor can be changed. For example, one or more lactate influencing parameters within the bioreactor can be selectively controlled in order to control lactate concentration. The condition being changed can include pH, carbohydrate concentrations such as glucose concentration, amino acid concentration, such as glutamate concentration and/or asparagine concentration, or the like. The pH of the cell culture can be changed by adding an acid or base to the cell culture, such as feeding carbon dioxide gas through the sparger and/or adding sodium bicarbonate to the cell culture. Carbohydrate concentration and/or amino acid concentration within the cell culture can be changed and modified by changing the nutrient media fed being feed to the bioreactor 10.

In one embodiment, for instance, in addition to lactate concentration, glutamate concentration can be monitored and fed to the controller 60. Based upon the predictive lactate trajectory over the incubation period, the glutamate concentration can then be selectively controlled in order to maintain lactate concentration within desired limits. In an alternative embodiment, asparagine concentration can be monitored in conjunction with lactate concentration. Should any corrective action be needed in order to maintain the lactate concentration within preselected limits, the asparagine concentration can be controlled by increasing or decreasing the flow rate of asparagine to the bioreactor by either controlling the flow rate of the nutrient media or by separately controlling asparagine by itself. In one embodiment, glutamate concentration, asparagine concentration, or both glutamate concentration and asparagine concentration are monitored during the process in addition to monitoring and controlling pH. Monitoring and controlling pH in addition to one or more amino acids or one or more carbohydrates has been found to effectively maintain lactate concentration within carefully controlled limits.

As described above, in one embodiment, the lactate influencing parameter that is monitored can be controlled for having desirable effects on lactate concentration. In an alternative embodiment, however, a first lactate influencing parameter can be monitored while a second lactate influencing parameter may be controlled during the process in order to influence lactate concentrations.

The system and process of the present disclosure has been found to effectively control lactate concentration within a cell culture. For example, through the process of the present disclosure, the incubation period of the cell culture can end in a lactate consuming state and can be prevented from ending in a lactate accumulating state. Final lactate concentration of the cell culture will depend upon numerous factors and is primarily dependent upon the type of cell being propagated. In one embodiment, the final lactate concentration of the cell culture can generally be less than about 3 g/L, such as less than about 2.5 g/L, such as less than about 2 g/L, such as less than about 1.5 g/L, such as less than about 1 g/L.

Of particular advantage, the controller 60 can also include a robust predictive model that can not only be scalable for different bioreactor types and bioreactor volumes, but can also be effective against multiple and diverse cell lines. For instance, it was discovered that the predictive model is well suited for use against multiple cell lines when the predictive model uses more than one multivariate technique, such as when using two multivariate techniques or three multivariate techniques.

In addition to monitoring one or more lactate influencing parameters, the controller can control various other process conditions. For instance, the controller can be in communication and control thermocirculators, load cells, control pumps, and receive information from various sensors and probes. For instance, the controller may control and/or monitor the oxygen tension, the temperature, the agitation conditions, the pressure, foam levels, and the like. For example, the controller can receive temperature information and control fluids being feed to a water jacket surrounding the bioreactor for increasing or decreasing temperature.

Through the process of the present disclosure, cell cultures can be grown with excellent product characteristics. For instance, cell cultures can be grown with excellent viability characteristics. For example, viability can be measured by dividing the viable cell count with the total cell count, which are two parameters that can both be measured during the process. In accordance with the present disclosure, cell cultures can be grown in accordance with the present disclosure having a viability ratio as described above of greater than about 0.6, such as greater than about 0.7, such as greater than about 0.8, such as greater than about 0.9. In fact, the viability ratio can be greater than about 0.94, such as greater than about 0.96, such as greater than about 0.98.

In addition, it was unexpectedly discovered that the system and process of the present disclosure can increase titer productivity. In particular, it was discovered that cell cultures controlled in accordance with the process of the present disclosure can have increased product titer concentration in relation to an identical cell culture that is not controlled in accordance with the present disclosure and wherein both cell cultures terminate with exactly the same lactate concentration or terminate with lactate concentrations that are within 0.5 g/L of each other, such as within about 0.25 g/l of each other. This result is dramatic and unexpected.

The present disclosure may be better understood with reference to the following examples.

Example

Fed-batch process data across five clones was used to create a time-varying dynamic model for use in a predictive model programmed into a controller to predict lactate concentration days into the future from prescribed values of pH and nutrient volume. After day three in the incubation period, the predictive model determined the optimum values for pH and nutrient volume to employ over a control horizon that best drives the lactate concentration to a prescribed set point over the remainder of the run. These optimized values for pH and nutrient volume were employed for the following day. The process was then repeated at the end of each day after inputting lactate concentration. The cell culture propagated was a mammalian cell culture used to produce a protein product. Eight different cultures where propagated. Four of the cell cultures were controlled in accordance with the present disclosure using the predictive model. The remaining four cell cultures were grown for purposes of comparison. Each of the cell cultures where grown in a 1 liter stirred tank bioreactor. Two of the cell cultures, however, were grown in a 1.5 liter stirred tank bioreactor and controlled with a predictive model in accordance with the present disclosure in order to demonstrate scalability. The following 8 sample cell cultures were propagated:

| Sample No. | Cell Culture Conditions | Controlled by predictive model ? |
| --- | --- | --- |
| 1 | Generic nutrient media | No |
| 2 | Modified and optimized nutrient media | No |
| 3 | Generic nutrient media | Yes |
| 4 | Generic nutrient media in 1.5 liter vessel | Yes |
| 5 | Modified and optimized nutrient media | No |
| 6 | Modified and optimized nutrient media and with increased pH | No |
| 7 | Modified and optimized nutrient media and with increased pH | Yes |
| 8 | Modified and optimized nutrient media and having a high initial glucose concentration in a 1.5 liter vessel | Yes |

As shown above, Sample Nos. 3, 4, 7, and 8 were controlled in accordance with the present disclosure.

More particularly, CHO-K1SV-derived clones stably expressing recombinant proteins were routinely cultured in suspension using commercially available CD-CHO AGT™. Inoculum trains were maintained in shake flasks in Kuhner incubators at 37° C., 5% $CO_2$, with no humidity control. Cells were regularly passaged to maintain exponential growth and expanded as needed to inoculate bench-scale bioreactors for experimentations described herein.

2-L scale glass bioreactors (BroadleyJames) were used to perform the fed-batch experiments. Bioreactor conditions such as pH, DO, and temperature set points varied according to the experimental plan. Culture pH was controlled using $CO_2$ sparge and base titrant addition. Dissolved oxygen was maintained at set points using oxygen sparge on demand. Culture temperature was controlled using a heating jacket. Concentrated glucose stock solutions were added as needed to maintain at least 0.5 g/L residual glucose concentration throughout the production run. Reactor experiments were performed for a 12-day duration.

Classification models were developed to predict the final lactate state from process data present through a specified end day (days 3, 4, and 5). For each end day considered, the following classification models were developed: linear discriminant analysis (LDA), classification trees, linear discriminant analysis applied to partial least squares scores (PLS-LDA), support vector machines (SVM) and logistic regression. Each individual model was computed from the batch-unfolded process data present in the training data set using functions (itcdiscr, fitctree, pisregress, itcsvm, itglm) from the Matlab statistics and machine learning toolbox (R2016b). A class threshold probability of 0.5 (i.e. 50%) was employed across classification models.

Models consistently yielding good classification accuracy across all end days included: PLS-LDA, LDA, classification trees and ensembles of these models. The classification models were able to accurately classify favorable and unfavorable lactate runs with validation accuracy ranging between 83% (Day 3) and 88% (Day 4 & 5). Though the day 4 and 5 models achieved equivalent validation classification accuracy in total, the day 4 ensemble model produced more consistent validation performance across clones. Attributes commonly appearing across models include metabolites (glutamate, glucose and glutamine) and attributes related to pH modulation ($CO_2$ sparge rate).

A model predictive controller (MPC) employing the time-varying ARX model was built in Matlab, with fmincon of the Matlab optimization toolbox (R2016b) used to minimize the cost function. Controller design parameters were initialized in simulation and tuned during preliminary experimental runs. Specifically, the desired lactate reference trajectory was set to zero for all days. The prediction and control horizons employed were 7 days and 1 day, respectively. The prediction horizon was decreased after day 3, as predictions were only required through day 10. Values for manipulated variables after day 10 were maintained at the last controller-prescribed values. A long prediction horizon served to ensure that the full effect of variations in the manipulated variables through run end were considered, whereas, a short control horizon ensured aggressive control action in the manipulated variables. As prediction accuracy did not dramatically degrade over longer prediction horizons, all prediction errors were considered to contribute equally to the minimized cost function (i.e. all $w_i^y$ were set to unity). Nutrient feed volume was constrained to remain between 1.8% and 3.6%, with maximum variations between days limited to +/−1.8% on days 3-6 and +/−1.0% otherwise. Bound constraints on pH were established at 6.7 and 7.2, with the maximum variation in pH between days set to +/−0.5.

The resulting MPC was employed in a series of experimental bioreactor runs to determine its efficacy in driving runs to a favorable lactate end state. Cell cultures employed in experiment were associated with a clone known to exhibit lactate accumulation in prior process development. Experimental MPC runs were conducted alongside two control runs: a basal run with known lactate accumulation behavior and a second for which supplemental asparagine included in the feed achieves a favorable lactate end state under normal operating conditions. In this set of experiments, variations in pH and nutrient feed volume were employed at the original reactor working volume (1 L) as well as a scale-up working volume of 1.5 L. Both control runs performed as expected, with the basal and asparagine-supplemented runs ending in unfavorable and favorable lactate states, respectively. MPC runs, with control initiated at the end of day 3, resulted in the cell culture achieving a favorable lactate end state with substantially lower lactate concentrations than the basal run.

A set of experiments also evaluated the ability of MPC to compensate for lactate-inducing disturbances in pH and glucose concentration. Elevated pH or glucose levels were employed early in each run to produce elevated lactate concentration levels. The asparagine-supplemented feed was employed in all the runs of this experiment. Two control runs were employed: one with normal pH and glucose levels and a second with elevated pH level (7.2 with 0.15 deadband). One MPC run employed the same elevated pH level through day 3 as in the corresponding control run while the second MPC run had an increased initial glucose concentration. The MPC runs rejected the initial disturbances in pH and glucose, with both runs yielding lower end lactate concentrations than the elevated pH control run. Variations in other measured cell culture parameters followed similar trends to those evidenced in the initial experiments. In contrast to the prior runs, viable cell density for the MPC runs were similar to that evidenced for the control run without elevated pH. Increased nutrient feed volumes in the MPC runs resulted in increased ammonium ion concentration and delayed depletion of glutamate.

Figure 4:
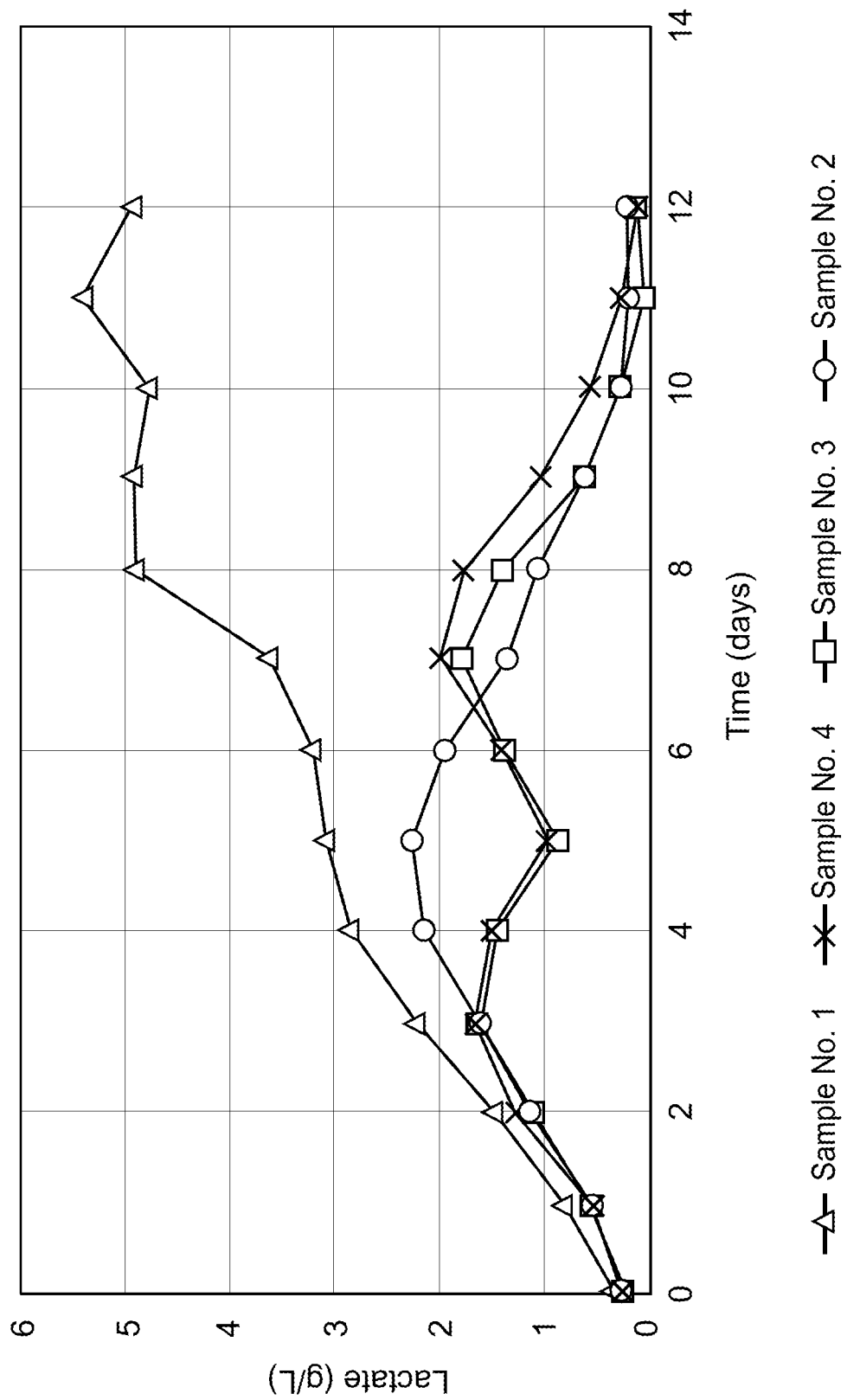
FIG. 4 through FIG. 19 are graphical representations of some of the results obtained in the example below.
Figure 5:
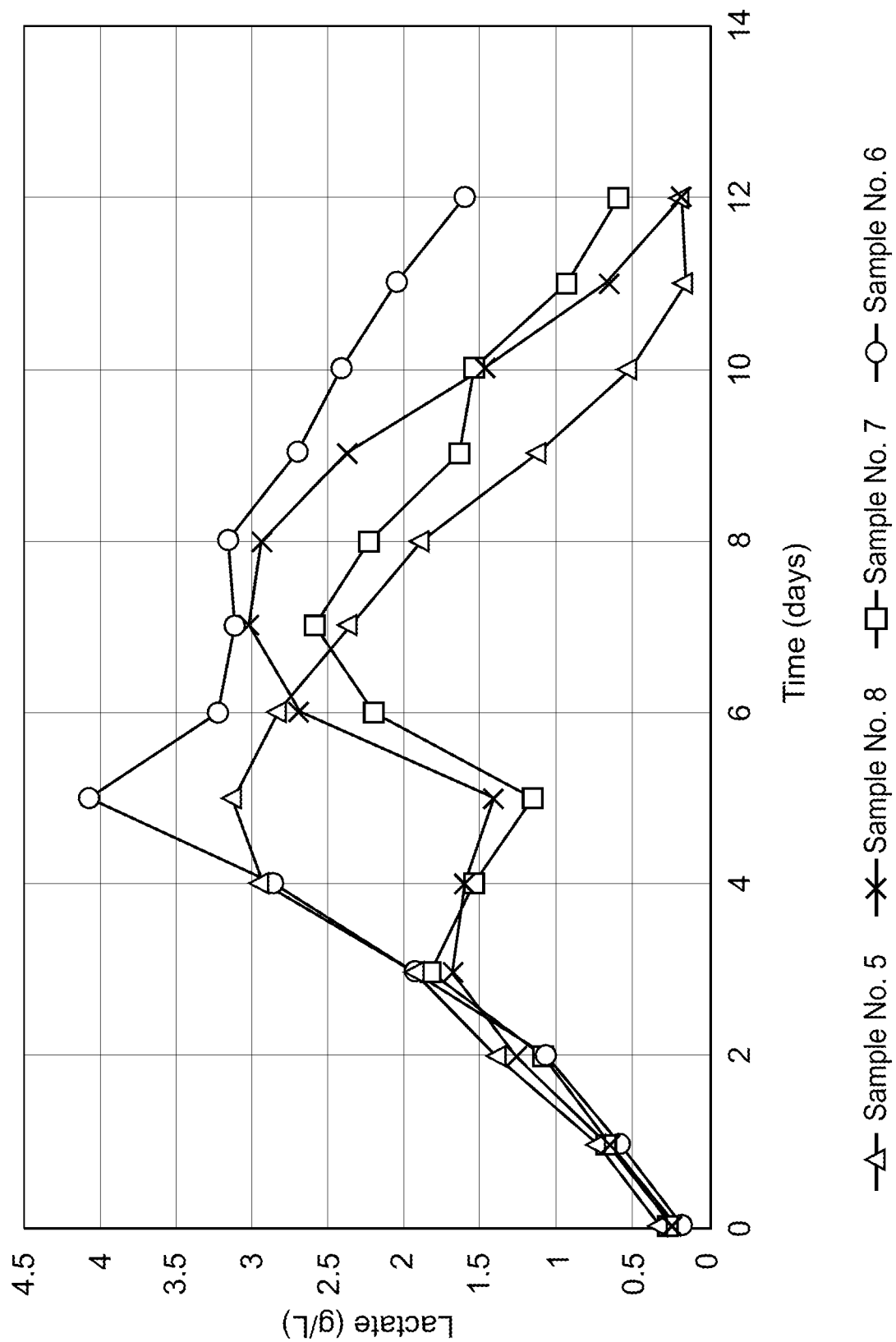

Referring to FIGS. 4 and 5, lactate concentration over a 12 day incubation period is shown. As illustrated, Sample No. 1 containing the generic nutrient media without controls produced very high lactate concentrations. Thus, in the past, the nutrient media was modified and optimized for the particular cell culture in order to control lactate levels. For instance, the nutrient media in Samples No. 2, 5 and 6 were all modified.

Sample Nos. 3 and 4 are cell culture runs where the cell culture was only fed the generic nutrient media but the cell culture was controlled in accordance with the present disclosure. As shown in FIG. 4, lactate levels were capable of being controlled without having to alter the nutrient media for the particular cell culture. FIGS. 4 and 5 demonstrate that the predictive model is capable of controlling lactate concentration over the incubation period.

Figure 6:
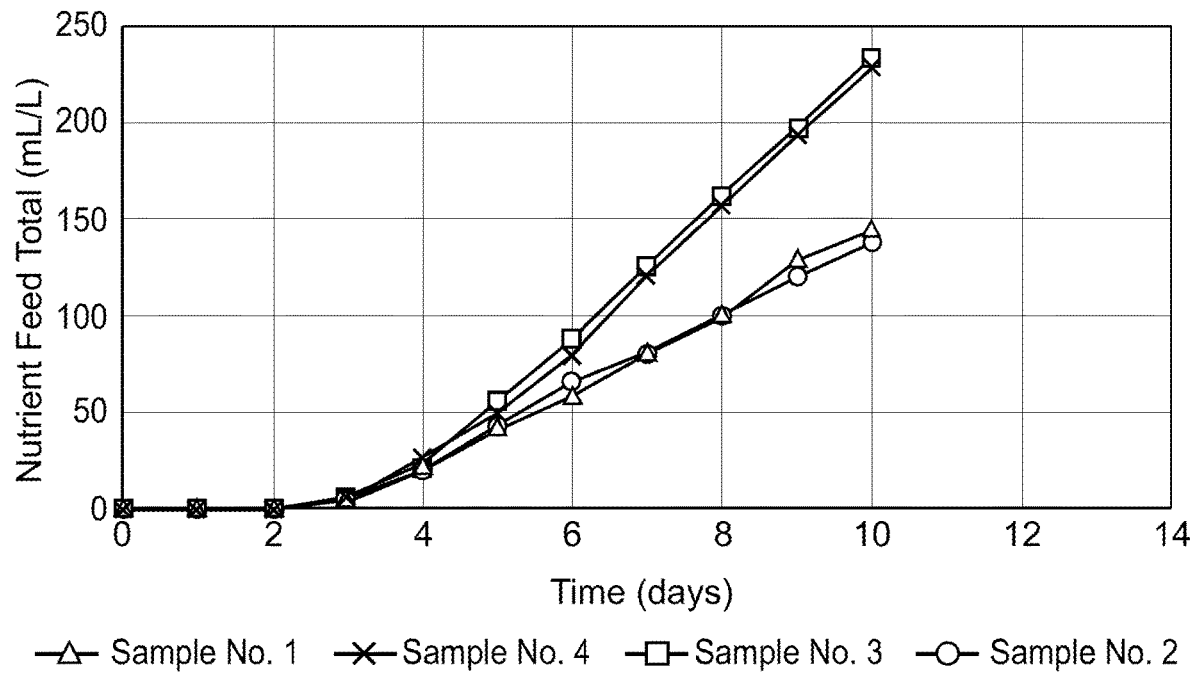
Figure 6:
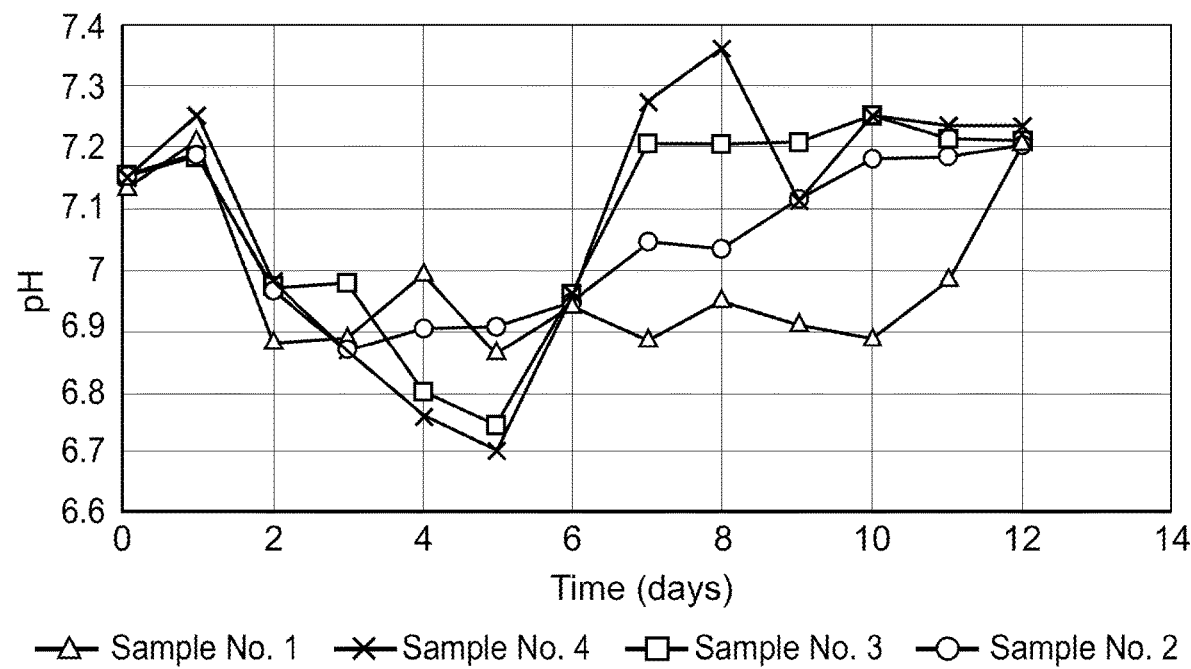
Figure 7:
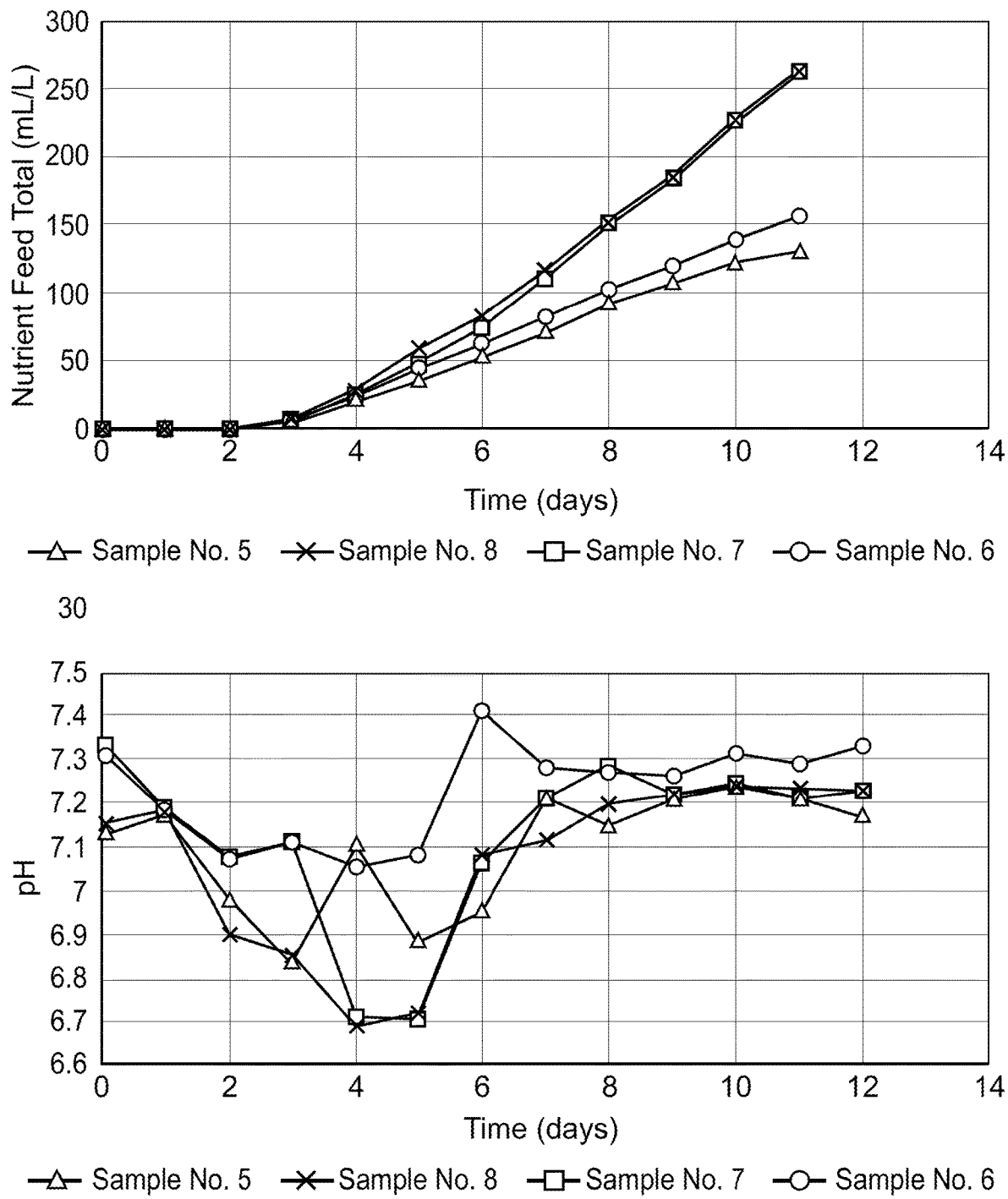

Referring to FIGS. 6 and 7, the nutrient feed and the pH are shown over the 12 day incubation period.

Figure 8:
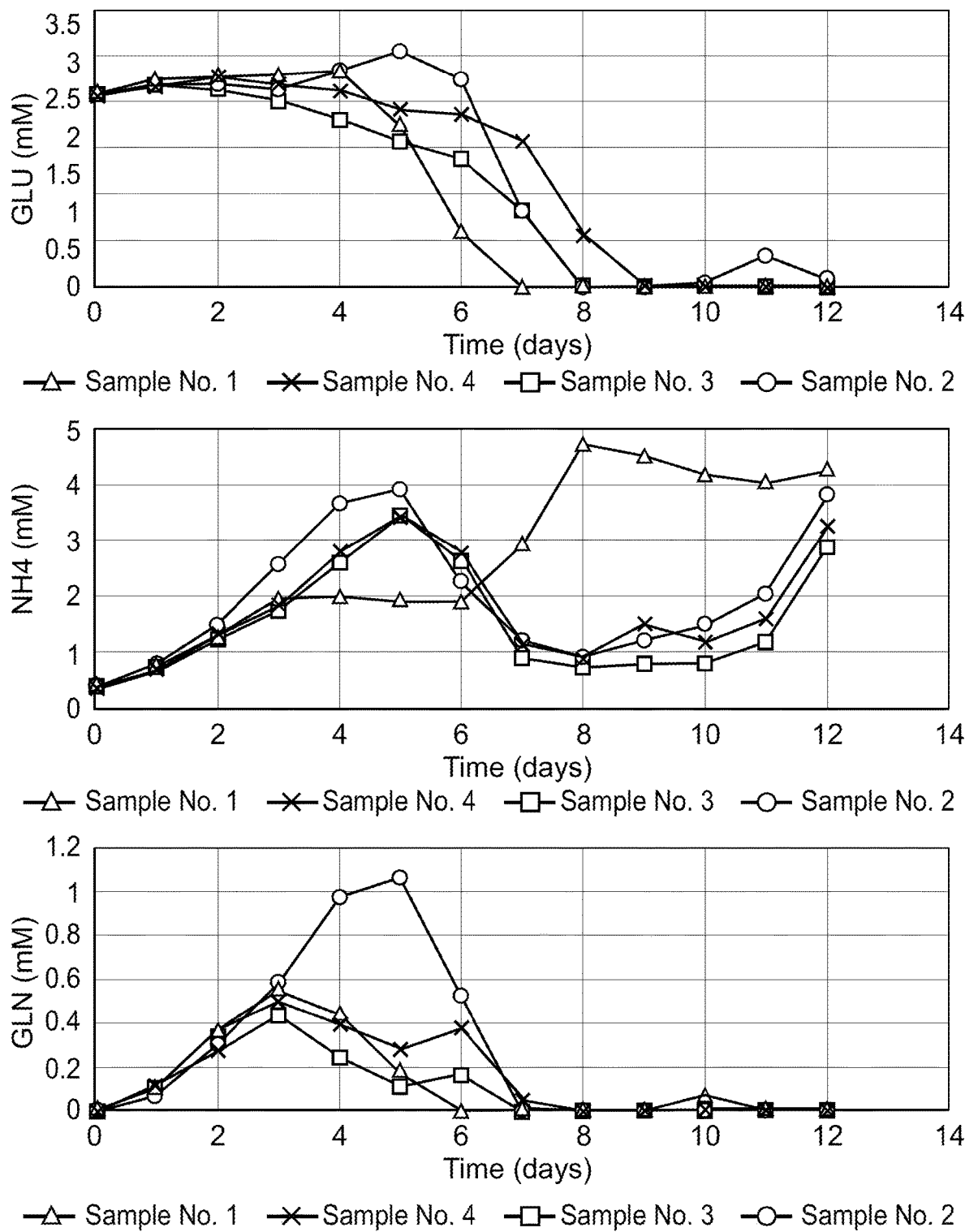
Figure 9:
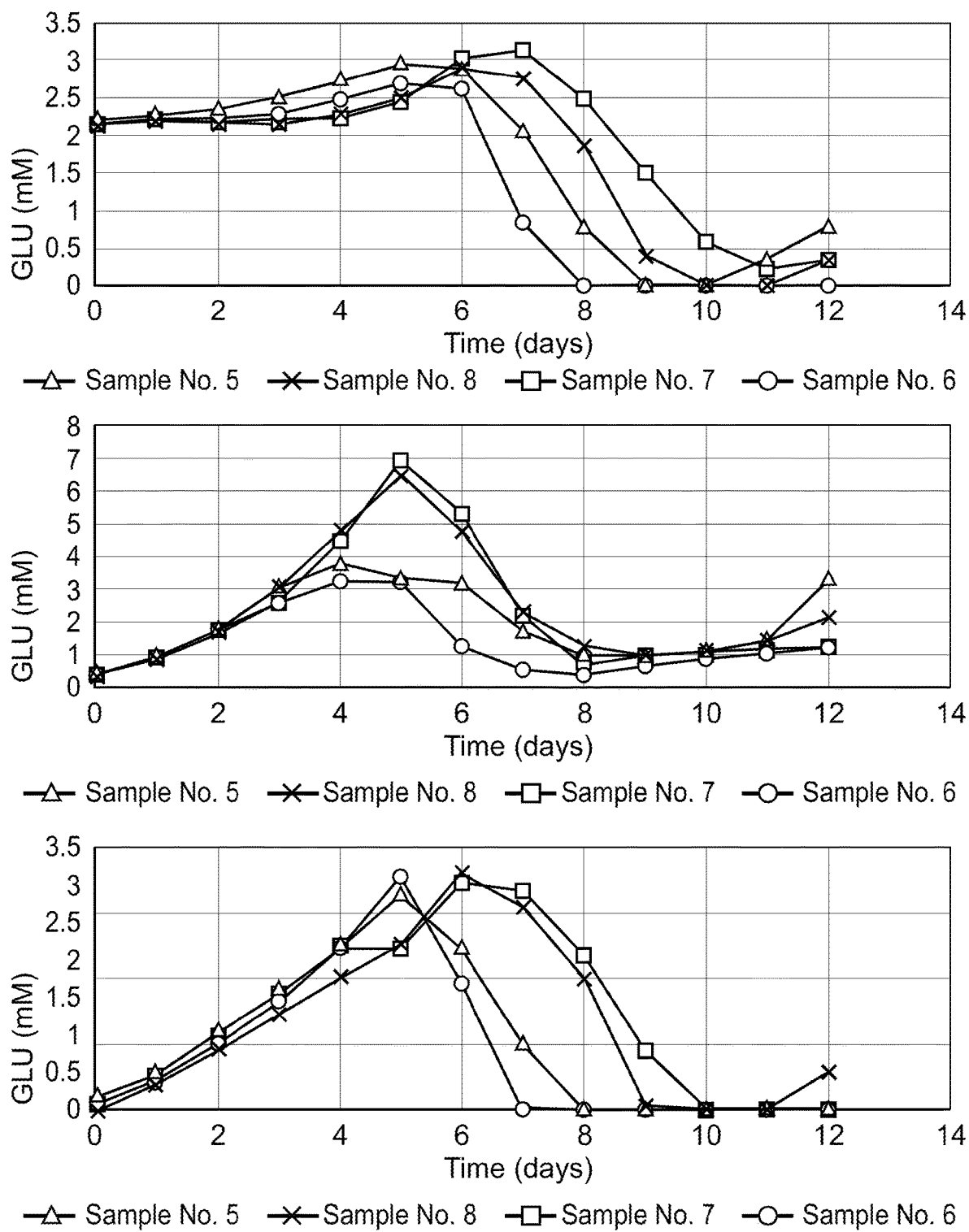
Figure 10:
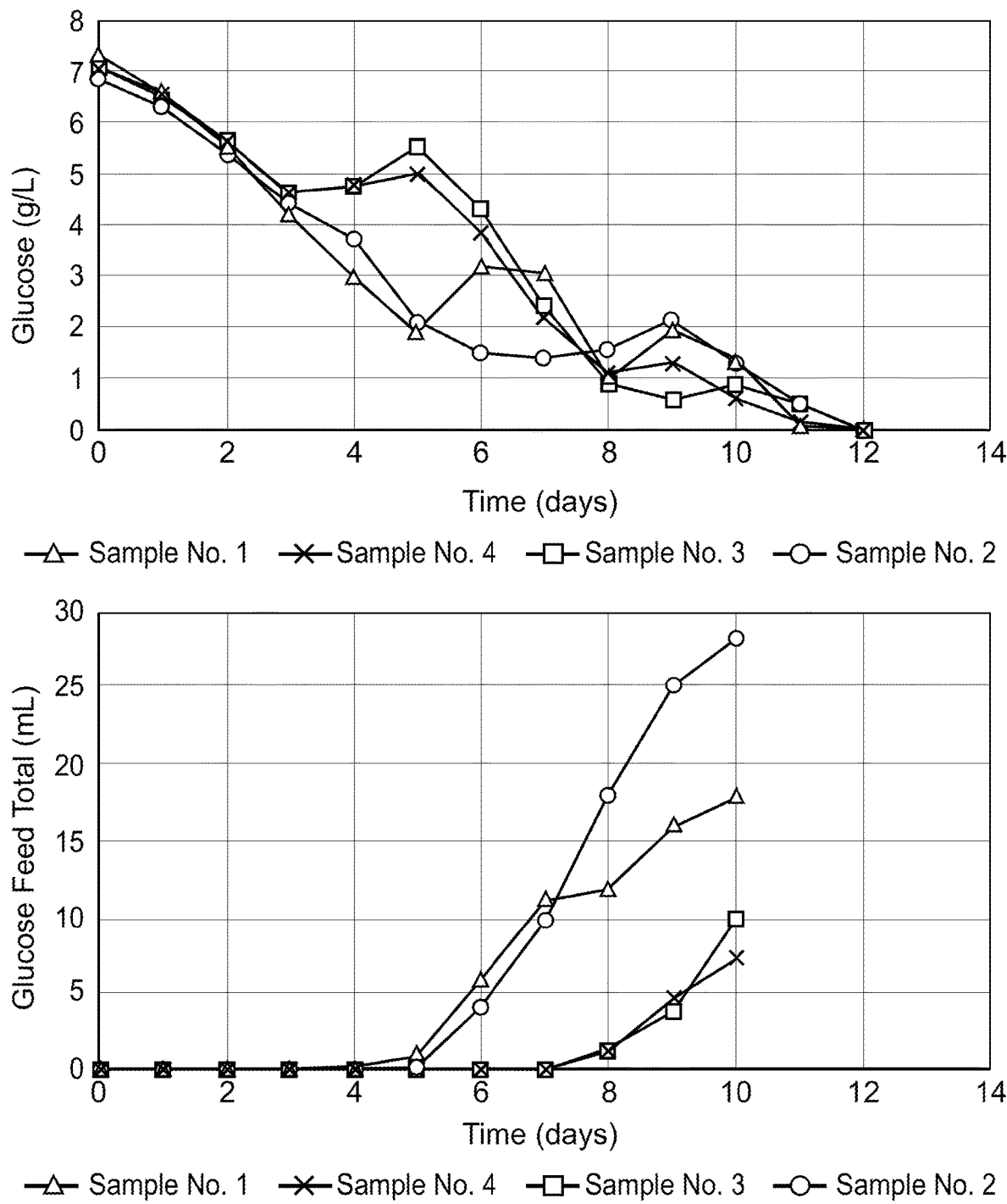
Figure 11:
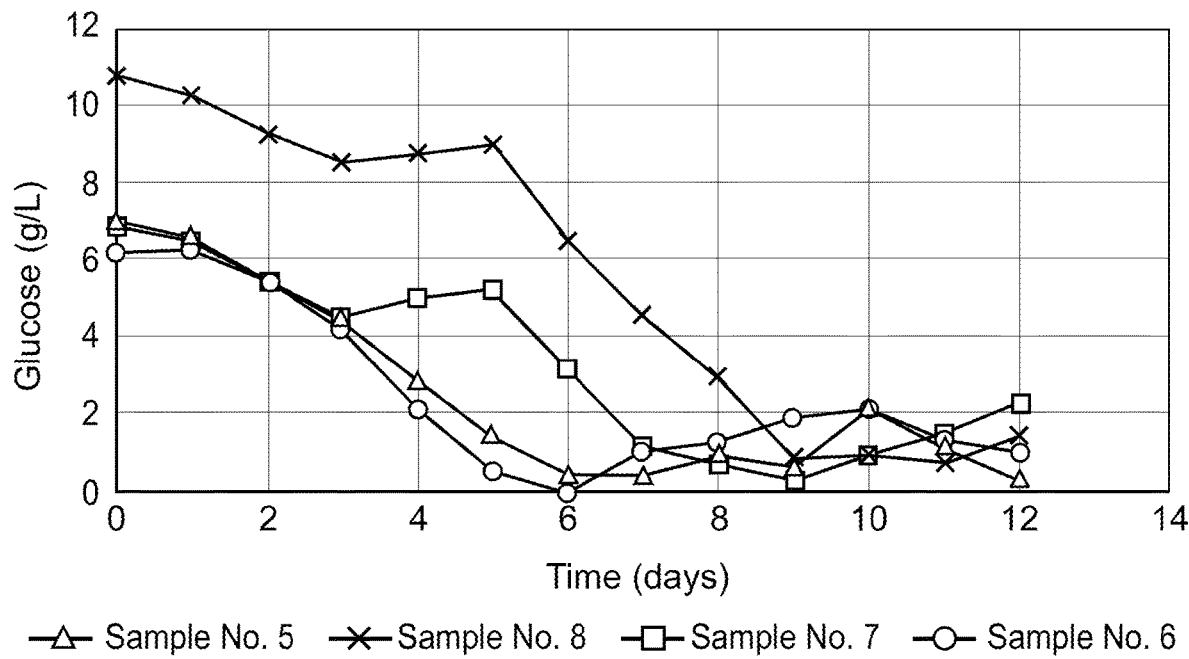
Figure 11:
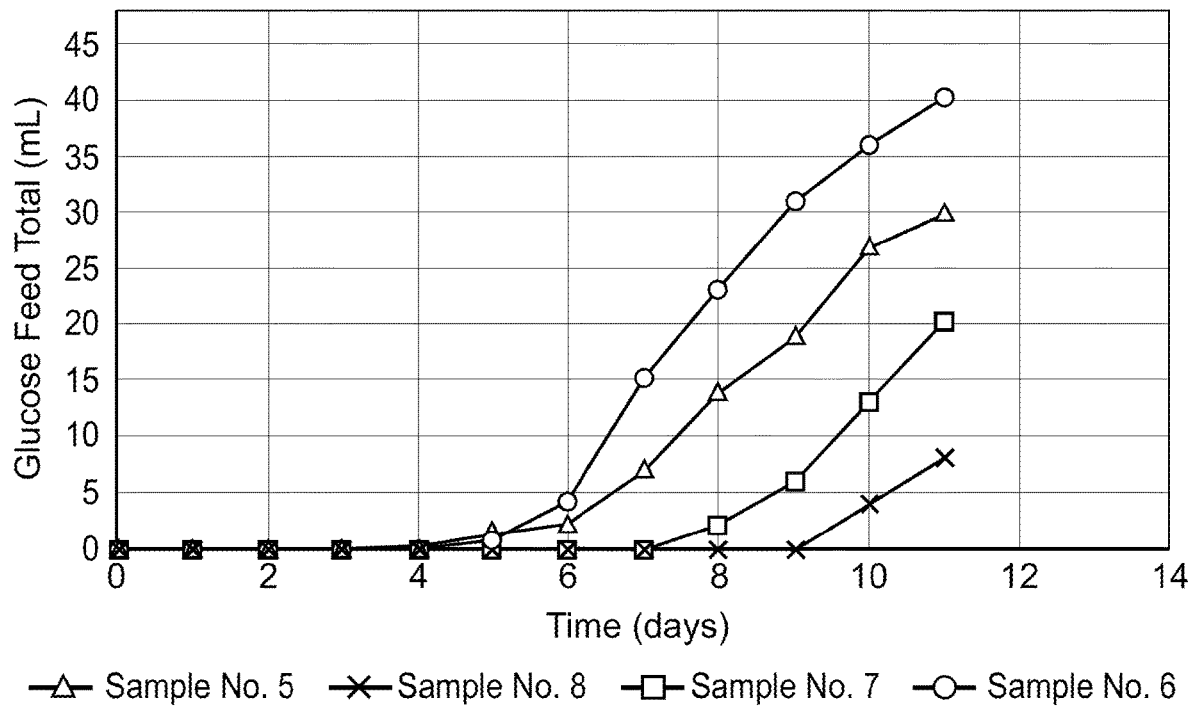

FIGS. 8 and 9 show ammonium concentration glutamate concentration and glutamine concentration over the 12 day incubation period. FIGS. 10 and 11, on the other hand, show glucose feed and glucose concentration within the cell culture.

Figure 12:
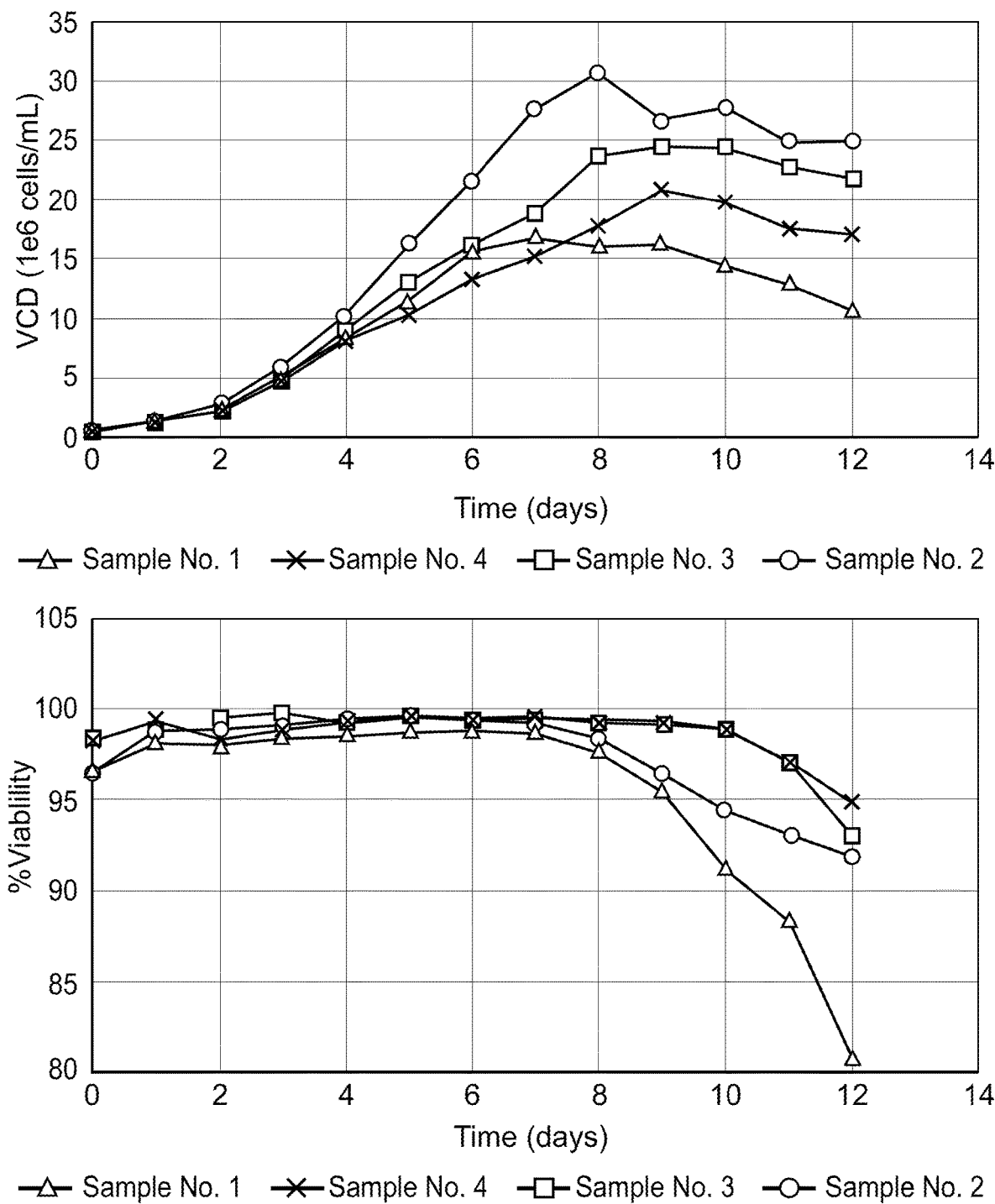
Figure 13:
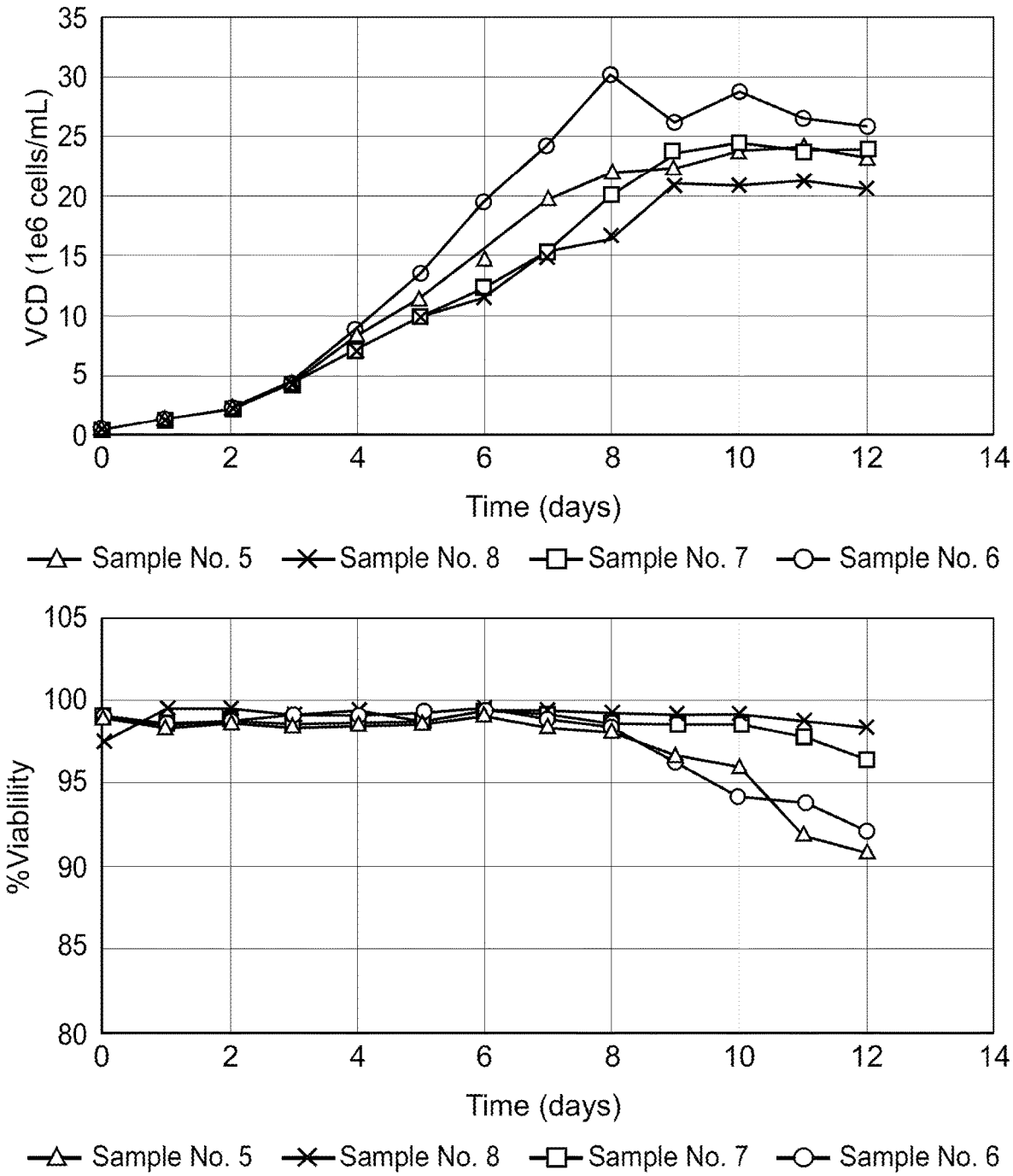
Figure 14:
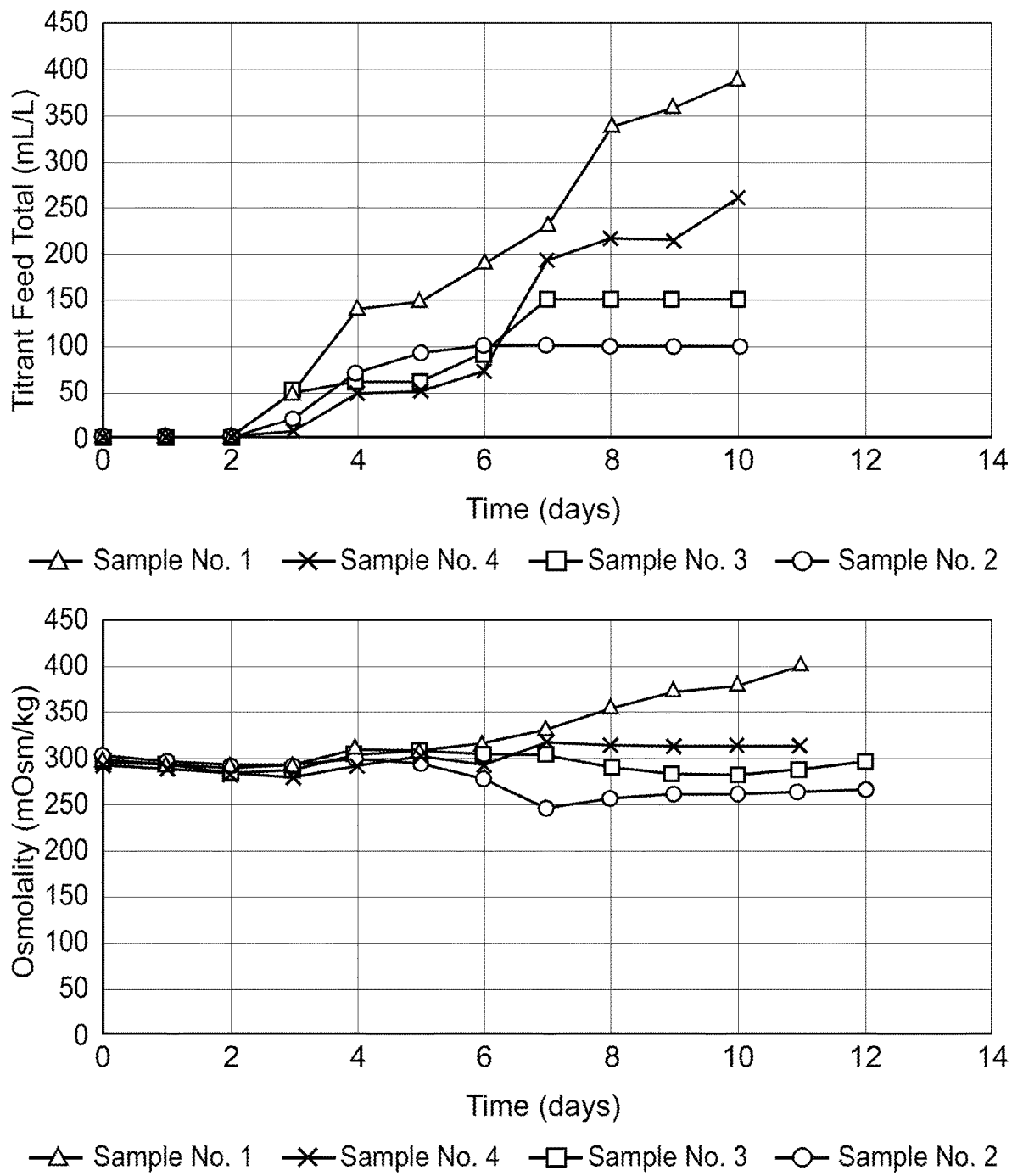
Figure 15:
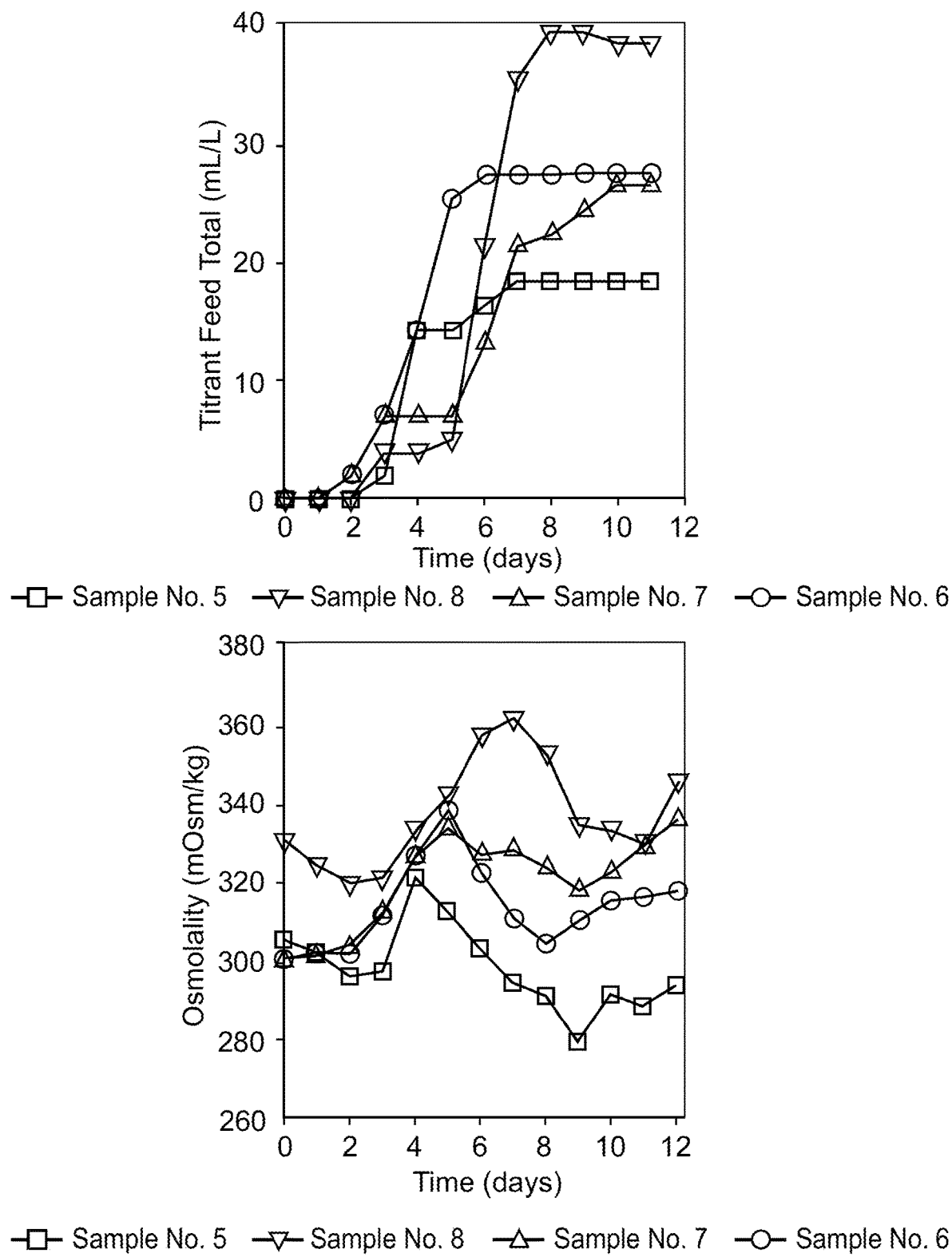

FIGS. 12 and 13 relate to product quality. The graphs show percent cell viability and the viable cell density. FIGS. 14 and 15, on the other hand, show titrant feed and osmolality.

FIGS. 16 through 19 illustrate how cell cultures controlled in accordance with the present disclosure actually produce greater product concentration even if the ending lactate concentration remains similar to the uncontrolled cell cultures.

In order to conduct titer analysis, standard curves were ran in triplicate, spread out through the course of the incubation period. These values were averaged to construct the standard curve used for quantification. Days 7 through 13 or 7 through 14 were analyzed.

Figure 16:
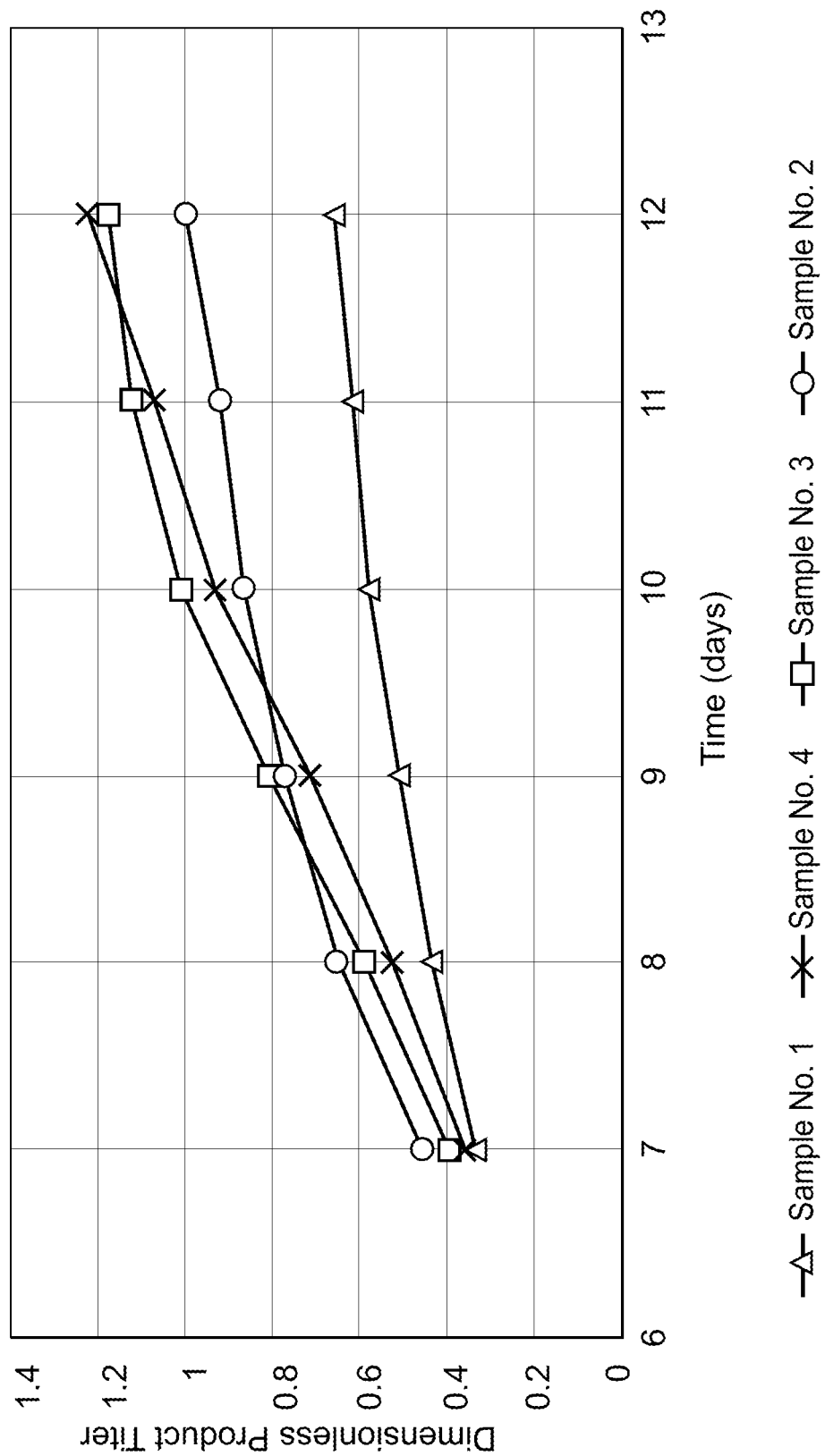
Figure 17:
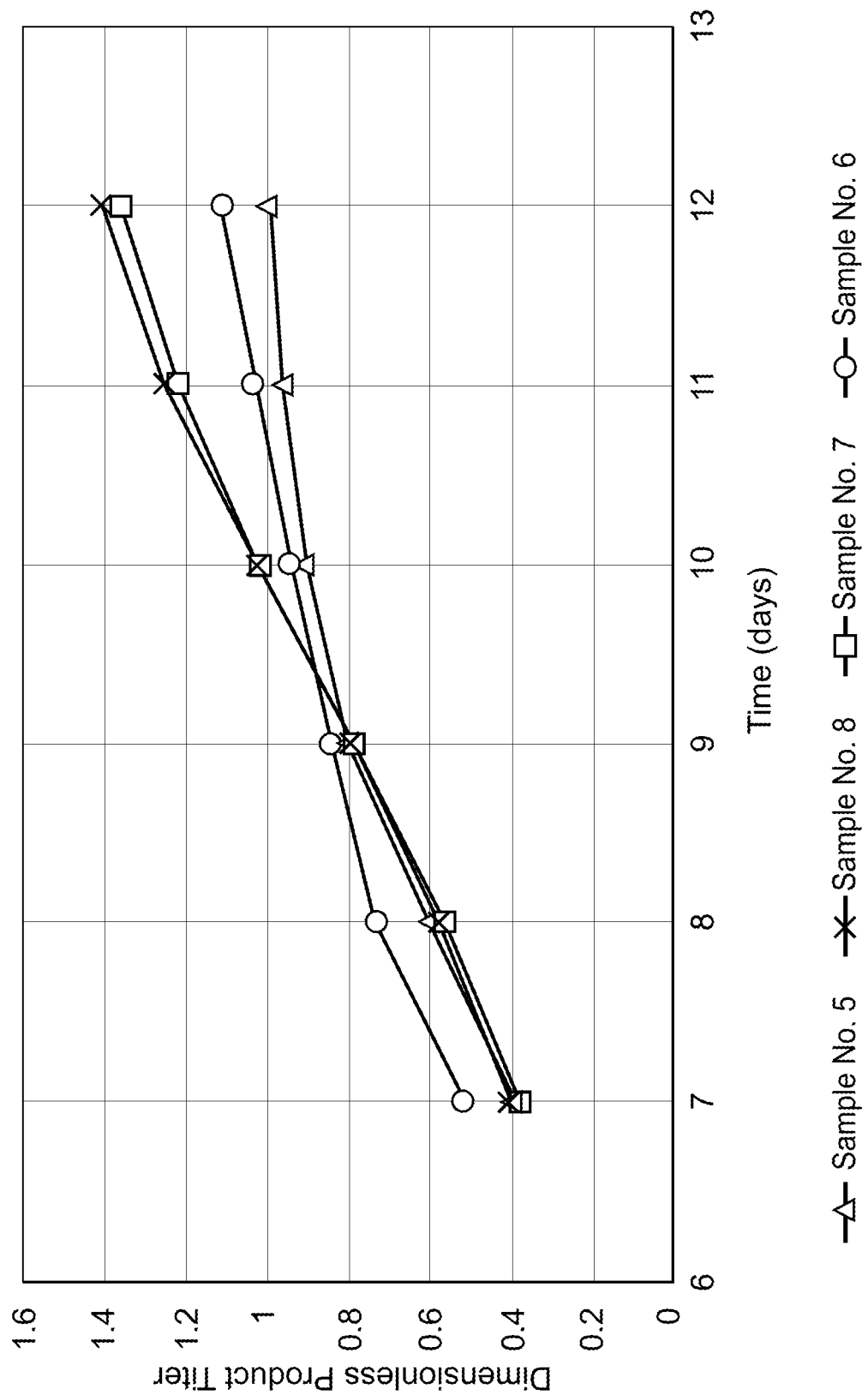
Figure 18:
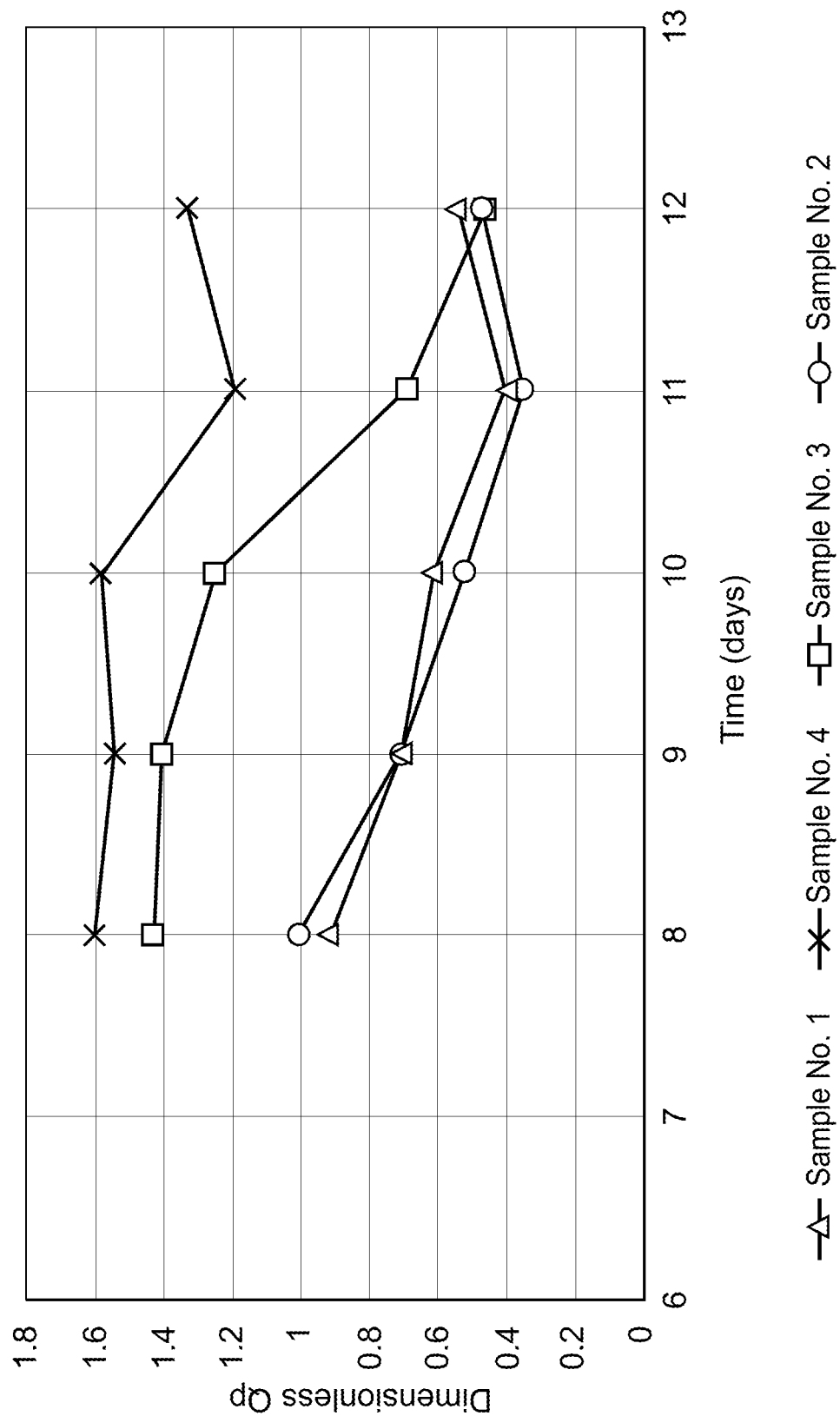
Figure 19:
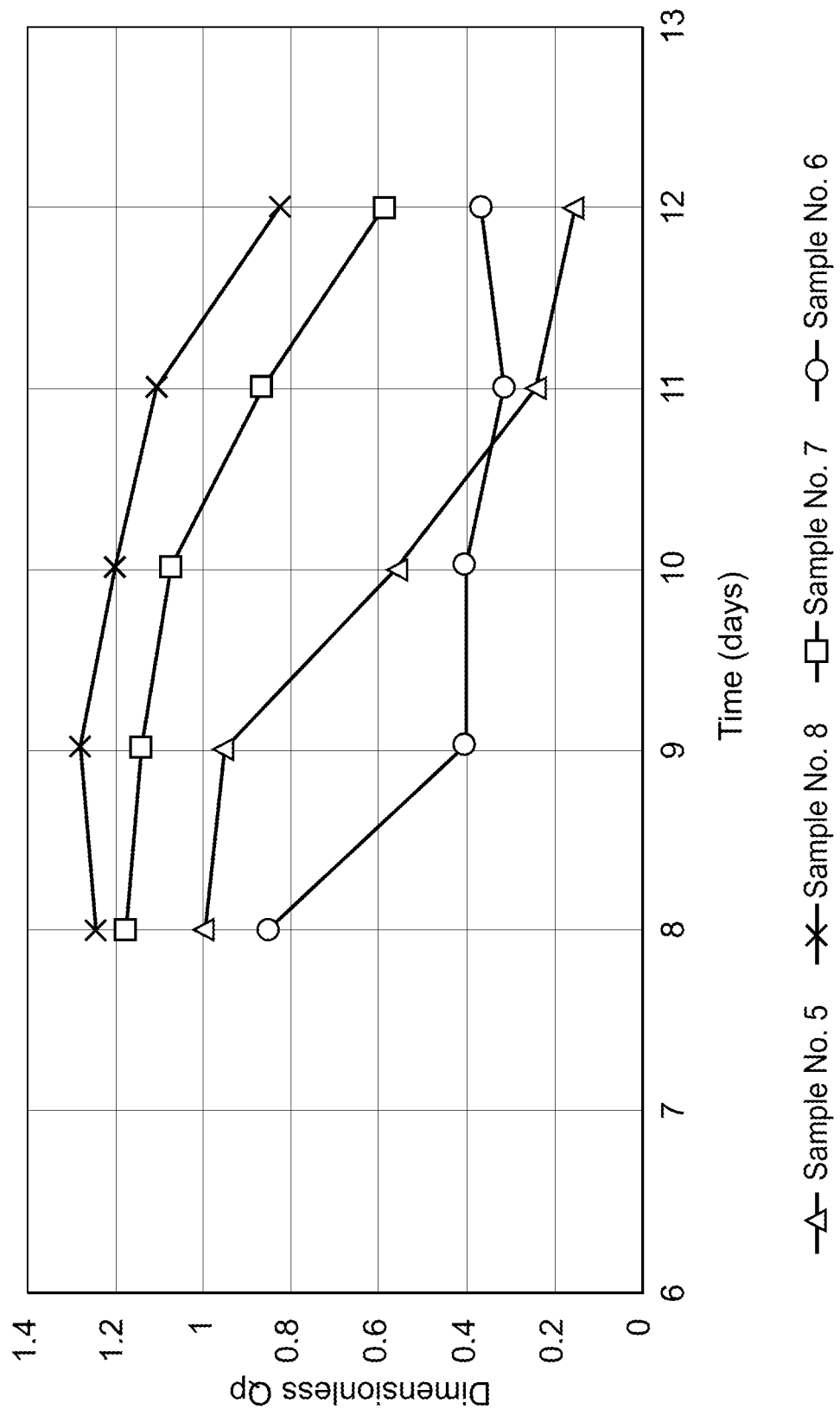

FIGS. 16 and 17 show product titer (normalized). As shown, cell cultures propagated in accordance with the present disclosure unexpectantly and dramatically had increased product titer or concentration. Similar results are illustrated in FIGS. 18 and 19, which illustrate amount of cells produced per day.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products-such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl1/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri*, and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica*, or *Schizosaccharomyces pombe*, Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*,or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g.

the *B. subtilis, B. amyloliquefaciens, B. licheniformis, B. natto*, or *B.megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12th Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin,Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enifavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, domase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestim, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpimase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MB-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, romidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 1311-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutanous injection, eczema), pitrakinra (inhaled dry powder, asthma), Multikine, RG-1068, MM-093, NB-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-g, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, S1-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP—HIP, SUN-11031, peptide YY [3-36](obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, FactorXII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S. pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RIT- UXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
|---|---|
| interferon gamma-1b | Actimmune ® |
| alteplase; tissue plasminogen activator | Activase ®/ Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/ Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |

TABLE I-continued

| Protein Product | Reference Listed Drug |
|---|---|
| Oprelvekin | Neumega ® |
| Filgrastim | Neupogen ® |
| Fanolesomab | NeutroSpec ™ (formerly LeuTech ®) |
| somatropin [rDNA] | Norditropin ®/ Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/ Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/ Growth factor | Type I alpha-interferon | Infergen |
| | Interferon-αn3 (IFNαn3) | Alferon N |
| | Interferon-β1a (rIFN- β) | Avonex, Rebif |
| | Interferon-β1b (rIFN- β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAh) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/ Protein vaccines/ Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tubingen) | Tandem scFv | CD28, MAPG | Retargeting of T cells to tumor | Phase II | Metastatic melanoma |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for propagating a cell culture comprising:
   determining a concentration of one or more quality attributes selected from the group consisting of lactate, a protein, glycan, a charge variant, an aggregate, disulfide oxidation, and a disulfide shuffling variant, in a cell culture;
   measuring a value of at least one attribute influencing parameter within the cell culture;
   sending the quality attribute concentration and the value of the at least one attribute influencing parameter measurement to a controller, the controller including a predictive model that is configured to calculate a future concentration of the quality attribute in the cell culture based at least in part on the value of the at least one attribute influencing parameter;
   running simulations on an optimizer to calculate future concentrations of the quality attribute based on manipulation of the attribute influencing parameter within the cell culture; and
   the controller selectively changing at least one condition within the cell culture based upon the simulations of the calculated future concentration of the quality attribute in the cell culture for maintaining the quality attribute concentration within preset limits.

2. A process as defined in claim 1, wherein the attribute influencing parameter is selected from the group consisting of pH, glutamate concentration, glucose concentration, asparagine concentration, temperature, and nutrient feed rate.

3. A process as defined in claim 1, wherein the predictive model calculates future concentration using at least two different multivariate methods.

4. The process as defined in claim 1, comprising measuring a change with time of the at least one attribute influencing parameter.

5. The process as defined in claim 1, wherein the controller operates in a closed loop control system, where adjustments to input and/or output devices connected to a bioreactor including the cell culture are completely automated.

6. A process for propagating a cell culture comprising:
   determining a concentration of lactate in a cell culture;
   measuring a value of at least one lactate influencing parameter within the cell culture;
   sending the lactate concentration and the value of the at least one lactate influencing parameter measurement to a controller, the controller including a predictive model that is configured to calculate a future concentration of lactate in the cell culture based at least in part on the value of the at least one attribute influencing parameter;
   running simulations on an optimizer to calculate future concentrations of lactate based on manipulation of the lactate influencing parameter within the cell culture; and
   the controller selectively changing at least one condition within the cell culture based upon the simulations of the calculated future concentration of lactate in the cell culture for maintaining lactate concentration within preset limits,
   wherein the cell culture has an incubation period prior to being harvested, and wherein the predictive model forecasts a final lactate concentration at the end of the incubation period.

7. A process as defined in claim 6, wherein the lactate influencing parameter comprises pH, glutamate concentration, glucose concentration, asparagine concentration, temperature, and/or nutrient feed rate.

8. A process as defined in claim 6, wherein at least two lactate influencing parameters are measured and the measured data are sent to the controller and used for calculating the future concentration of lactate in the cell culture.

9. A process as defined in claim 6, wherein the at least one condition is selectively changed by changing a nutrient media being fed to the cell culture.

10. A process as defined in claim 9, wherein the nutrient media comprises a carbohydrate source, an amino acid source, a vitamin, a lipid, a protein, a peptide, or mixtures thereof.

11. A process as defined in claim 9, wherein the nutrient media being fed to the cell culture is changed by changing a flow rate of the nutrient media to the cell culture.

12. A process as defined in claim 11, wherein in addition to changing the nutrient media being fed to the cell culture, a pH of the cell culture is also selectively changed in order to maintain lactate concentration within preset limits.

13. A process as defined in claim 6, wherein the at least one condition within the cell culture is selectively changed during the incubation period such that the final lactate concentration of the cell culture at the end of the incubation period is less than about 2 g/L.

14. A process as defined in claim 6, wherein the process results in an increase in titer concentration of the cell culture.

15. A process as defined in claim 6, wherein the cell culture contains mammalian cells.

16. A process as defined in claim 6, wherein the cell culture is propagated in a batch process for from about 12 hours to about 28 days and then harvested.

17. A process as defined in claim 16, wherein the lactate concentration in the cell culture is calculated for from about 12 hours to about 4 days, prior to the controller calculating a future concentration of lactate in the cell culture.

18. A process as defined in claim 16, wherein the batch process includes an incubation time prior to harvesting the cell culture, and wherein the lactate concentration is measured for from about 5% to about 40% of the incubation time prior to the controller calculating a future concentration of lactate in the cell culture.

19. A process as defined in claim 16, wherein the lactate concentration is calculated at least every 12 hours, all of the lactate concentration data being fed to the controller and wherein the controller is configured to repeatedly calculate the future concentration of lactate in the cell culture as further data is received.

20. A process as defined in claim 6, wherein the predictive model is based on comparing lactate concentration to prior reference data.

21. A process as defined in claim 6, wherein the future concentration of lactate is calculated by the predictive model from a square deviation of lactate concentration predicted from a prescribed reference trajectory.

22. A process as defined in claim 21, wherein the predictive concentration of lactate is also calculated based on square deviation in changes of the at least one lactate influencing parameter.

23. A process as defined in claim 21, wherein the predictive model applies weighting to the difference between a predicted output and the referenced trajectory for each day.

24. A process as defined in claim 6, wherein the future concentration of lactate is calculated using one or more techniques selected from partial squares analysis, classification trees, support vector determinations, linear discriminant analysis, or mixtures thereof.

25. A process as defined in claim 6, wherein the future concentration of lactate is calculated by the controller using a reduced order time varying autoregressive exogenous model.

26. A system for propagating a cell culture comprising:
a bioreactor defining a hollow interior for receiving a cell culture, the bioreactor including a plurality of ports for feeding and/or removing materials from the hollow interior; a nutrient media feed for feeding a nutrient media to the hollow interior of the bioreactor, the nutrient media feed being in fluid communication with at least one of the ports on the bioreactor;
a controller configured to receive lactate concentration measurements of a cell culture contained in the bioreactor, the controller also being configured to receive measurements of at least one lactate influencing parameter, the controller including a predictive model that is configured to calculate a future concentration of lactate in a cell culture contained in the bioreactor, the controller being configured to run simulations on an optimizer to calculate simulated future concentrations of the lactate concentrations based on manipulation of the nutrient media within the cell culture, the controller being configured to control the nutrient media feed for selectively increasing or decreasing flow of a nutrient media into the bioreactor based upon the simulations of the predicted lactate concentration for maintaining the lactate concentration within preset limits.

27. The process as defined in claim 6, comprising measuring a change with time of the at least one lactate influencing parameter.

28. The process as defined in claim 6, wherein the controller operates in a closed loop control system, where adjustments to input and/or output devices connected to a bioreactor including the cell culture are completely automated.

* * * * *